(12) United States Patent
Slaga et al.

(10) Patent No.: US 9,789,272 B2
(45) Date of Patent: Oct. 17, 2017

(54) BRIDLE DEVICE AND METHOD

(71) Applicant: Abeon Medical Corporation, Brecksville, OH (US)

(72) Inventors: Allison Slaga, Brecksville, OH (US); Matthew Thompson, Broadview Heights, OH (US)

(73) Assignee: Applied Medical Technology, Inc., Brecksville, OH (US)

( * ) Notice: Subject to any disclaimer, the term of this patent is extended or adjusted under 35 U.S.C. 154(b) by 865 days.

(21) Appl. No.: 13/964,985

(22) Filed: Aug. 12, 2013

(65) Prior Publication Data

US 2014/0041666 A1 Feb. 13, 2014

Related U.S. Application Data

(60) Provisional application No. 61/682,112, filed on Aug. 10, 2012, provisional application No. 61/682,115, filed on Aug. 10, 2012.

(51) Int. Cl.
*A61M 16/06* (2006.01)
*A61M 16/04* (2006.01)
*A61M 25/02* (2006.01)

(52) U.S. Cl.
CPC .... *A61M 16/0683* (2013.01); *A61M 16/0461* (2013.01); *A61M 16/0488* (2013.01);
(Continued)

(58) Field of Classification Search
CPC .......... A61M 16/0683; A61M 16/0488; A61M 16/0497; A61M 16/0461; A61M 16/0666
See application file for complete search history.

(56) References Cited

U.S. PATENT DOCUMENTS 3,420,237 A 1/1969 Fortay
3,568,678 A 3/1971 Pourquier et al.
(Continued)

FOREIGN PATENT DOCUMENTS

FR 1336296 8/1963
JP 2004508108 A 3/2004
(Continued)

OTHER PUBLICATIONS

Dominguez, E., "Carbon Dioxide Monitoring during Deep Conscious Sedation . . . ," Anesthesiology 1999, vol. 91, No. 4, pp. 1177-1178, Oct. 1999.
(Continued)

*Primary Examiner* — Theodore Stigell
(74) *Attorney, Agent, or Firm* — Calfee, Halter & Griswold LLP

(57) ABSTRACT

The present application discloses a bridle device and a method of placing a bridle on a person using the bridle device. In one exemplary embodiment, the bridle device comprises a retrieval portion and a delivery portion. The delivery portion has a retrieval member and a retrieval magnet attached to the retrieval member. The delivery portion has a delivery member and a delivery magnet that is movable relative to a distal portion of the delivery member. In certain embodiments, the delivery portion has a delivery tube and a delivery magnet attached to a flexible elongated member received in the delivery tube. The delivery magnet is movable relative to a distal portion of the delivery tube and both poles of the delivery magnet are exposed outside of the delivery tube.

31 Claims, 26 Drawing Sheets

(52) U.S. Cl.
CPC ..... *A61M 16/0497* (2013.01); *A61M 16/0666* (2013.01); *A61M 2025/0226* (2013.01)

(56) References Cited

U.S. PATENT DOCUMENTS

| | | | |
|---|---|---|---|
| 3,776,222 | A | 12/1973 | Smiddy |
| 4,778,448 | A | 10/1988 | Meer |
| 4,821,715 | A | 4/1989 | Downing |
| 4,932,943 | A | 6/1990 | Nowak |
| 5,097,827 | A | 3/1992 | Izumi |
| 5,185,005 | A * | 2/1993 | Ballantyne ............ A61M 25/02 128/207.18 |
| 5,492,538 | A | 2/1996 | Johlin, Jr. |
| 5,692,506 | A | 12/1997 | Linder |
| 5,752,511 | A | 5/1998 | Simmons |
| 5,937,858 | A | 8/1999 | Connell |
| 6,098,617 | A | 8/2000 | Connell |
| 6,159,158 | A | 12/2000 | Lowe |
| 6,173,199 | B1 | 1/2001 | Gabriel |
| 6,394,093 | B1 | 5/2002 | Lethi |
| 6,408,850 | B1 | 6/2002 | Sudge |
| 6,464,668 | B1 | 10/2002 | Pace |
| 6,488,664 | B1 | 12/2002 | Solomon et al. |
| 6,631,715 | B2 * | 10/2003 | Kirn .................. A61M 16/0488 128/200.24 |
| 6,837,237 | B2 | 1/2005 | Kirn |
| 7,534,228 | B2 | 5/2009 | Williams |
| 7,604,627 | B2 | 10/2009 | Kojouri |
| 8,020,558 | B2 | 9/2011 | Christopher |
| 8,056,562 | B2 | 11/2011 | Sherman |
| 2002/0026936 | A1 | 3/2002 | Kirn |
| 2004/0069309 | A1 | 4/2004 | Kirn |
| 2004/0099273 | A1 | 5/2004 | Wright |
| 2004/0231675 | A1 | 11/2004 | Lyons |
| 2005/0236001 | A1 * | 10/2005 | Williams .............. A61M 25/02 128/207.18 |
| 2005/0240147 | A1 | 10/2005 | Makower |
| 2006/0189947 | A1 | 8/2006 | Gilbert et al. |
| 2006/0283464 | A1 | 12/2006 | Dunlap |
| 2008/0006275 | A1 | 1/2008 | Nickelson et al. |
| 2008/0142019 | A1 | 6/2008 | Lewis et al. |
| 2008/0216826 | A1 | 9/2008 | Boyden et al. |
| 2009/0248057 | A1 | 10/2009 | Kotler |
| 2010/0242967 | A1 | 9/2010 | Burbank |
| 2012/0080037 | A1 | 4/2012 | Guyuron et al. |
| 2013/0019872 | A1 | 1/2013 | Guyuron |
| 2013/0087152 | A1 | 4/2013 | Kirn |
| 2013/0152940 | A1 | 6/2013 | Larson |

FOREIGN PATENT DOCUMENTS

| | | |
|---|---|---|
| WO | 9920334 | 4/1999 |
| WO | 9929358 | 6/1999 |
| WO | 0220082 | 3/2002 |

OTHER PUBLICATIONS

Dominguez, E., "Another Use for Nasopharyngeal Airway," Anesthesiology 2000, vol. 93, No. 1, pp. 298-299, Jul. 2000.
Lee, Christopher R., "Who Nose Where the Airway Is?", Agency for Healthcare Research and Quality (AHRQ) WebM&M, Cases & Commentary, Oct. 2009. http://www.webmm.ahrq.gov.
AMT Bridle Nasal Tube Retaining System brochure, 4 pgs., Applied Medical Technology, Inc., copyright 2010. www.appliedmedical.net.
Kotler, R., et al., "Introducing . . . The Kotler Nasal Airway™", The Kotler Nasal Airway Official Website, "A Strategy and New Device to Ensure Patient Safety . . . ," copyright 2011. www.kotlernasalairway.com.
International Search Report and Written Opinion from PCT/US2013/046213, dated Oct. 21, 2013.
Rhino Rocket® with Applicator, Shipped Medical Technologies Incorporated on-line catalog, vol. IX, p. 11, copyright 2013 www.shippertmedical.com.
Rapid Rino® 900, ArthroCare Corporation, on-line Technique Guide, 2 pgs., copyright 2009. www.arthrocareENT.com.
Office Action from U.S. Appl. No. 13/839,012 dated Apr. 21, 2016.
Extended search report from European Patent Application No. 13807038.8 dated May 18, 2016.
Response to EP Communication dated Feb. 12, 2016 in EP Application No. 13 827 165.5 dated Aug. 18, 2016.
International Search Report and Written Opinion from International Application No. PCT/US2013/05467, date of mailing Apr. 7, 2014.
Search Report from European Patent Application No. 13827165.5 dated Jan. 27, 2016.
Levenson, Albert, "Feeding Tube Anchor," 5 Nutritional Support Services, 8, pp. 40-42 (1985).
Barrocas, Albert, "The Bridle:Increasing the Use of Nasoenteric Feedings," Nutritional Support Services, vol. 2, No. 8, Aug. 1982, pp. 8-10.
McGuirt, W. Frederick et al., "Securing of Intermediate Duration Feeding Tubes" The Laryngoscope 90:1980, pp. 2046-2048.
Meer, Jeffrey A., A New Nasal Bridle for Securing Nasoentereal Feeding Tubes, 13 J. Parenteral & Enteral Nutrition, 331, 331-33 (1989).
Office Action from U.S. Appl. No. 13/839,012 dated Dec. 16, 2016.
Notice of Reasons for Rejection for Japanese Patent Application No. 2015-525757 dated Jun. 1, 2017.

* cited by examiner

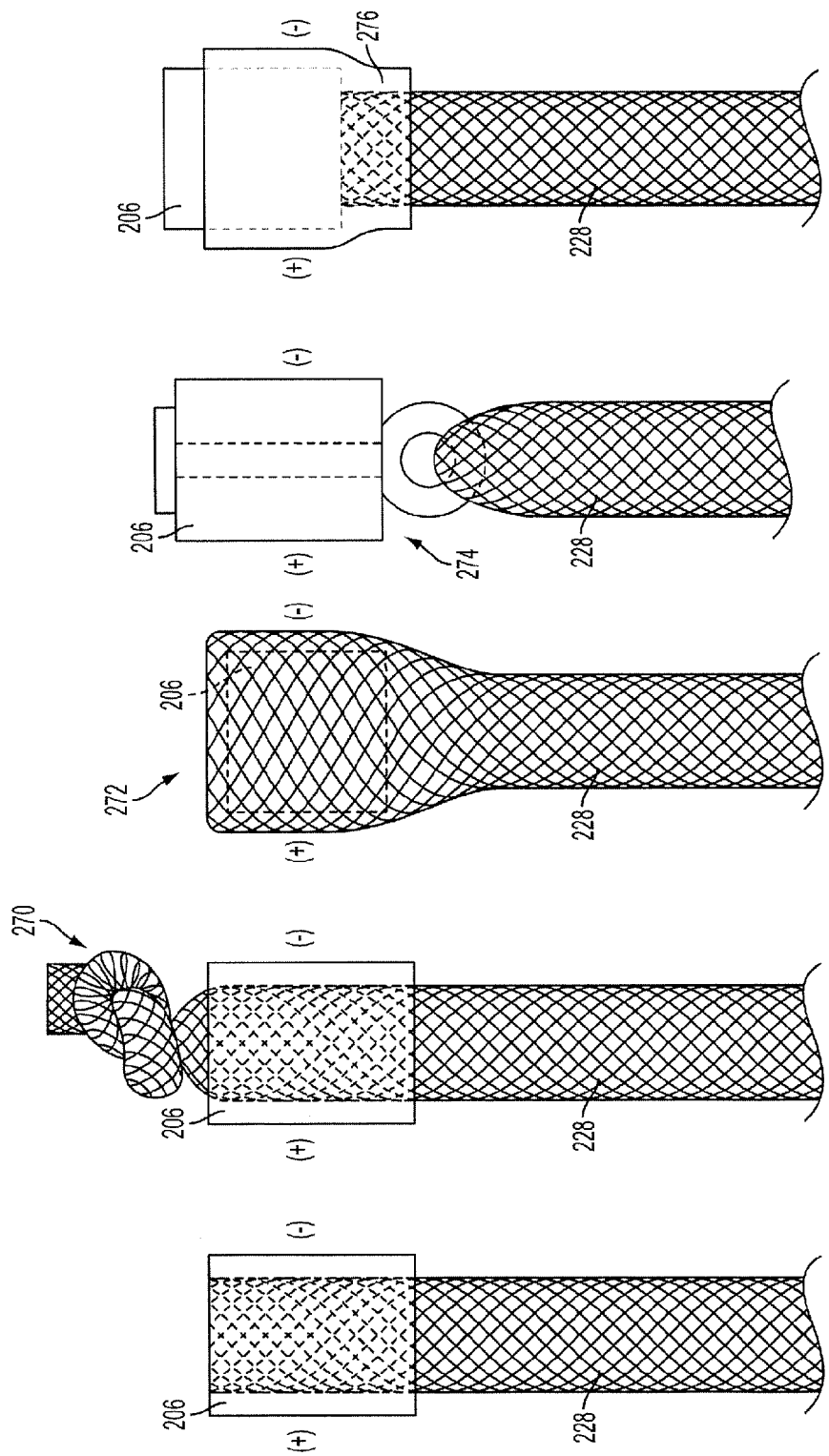

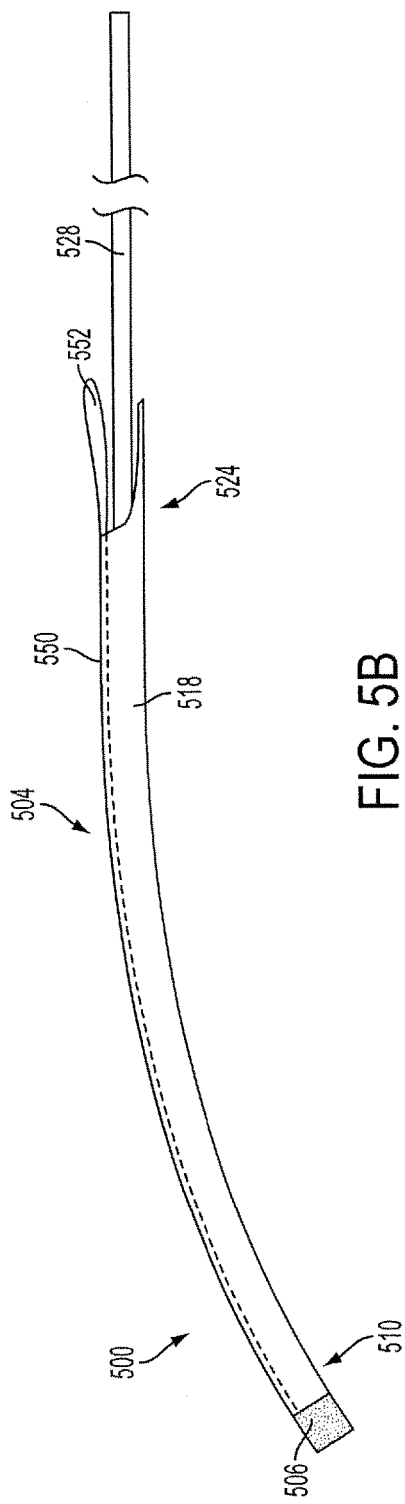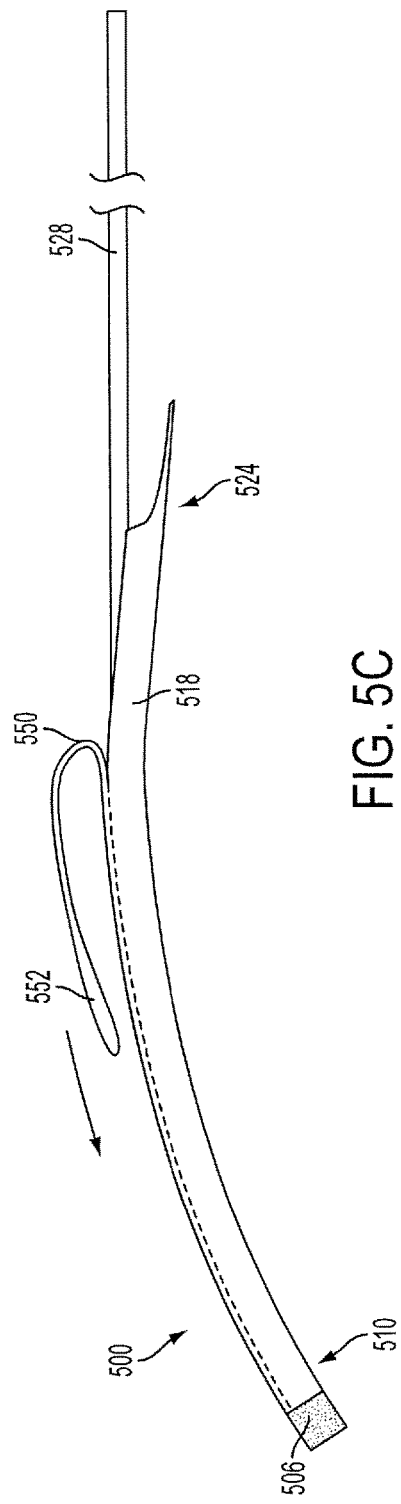

BRIDLE DEVICE AND METHOD

CROSS REFERENCE TO RELATED APPLICATIONS

This application is a U.S. Non-Provisional Patent Application which claims priority to U.S. Provisional Patent Application No. 61/682,112, filed on Aug. 10, 2012 and titled "Bridle Device," and U.S. Provisional Patent Application No. 61/682,115, filed on Aug. 10, 2012 and titled "Nasal Tube," both of which are hereby incorporated by reference in their entirety.

BACKGROUND

Nasal tubes are often secured to the patient to prohibit removal or displacement of the tube. A conventional method of securing a nasal tube to a patient is with a magnetic bridle system. Conventional magnetic bridle systems generally have a catheter that delivers a magnet to the nasopharnyx of a patient. The catheter is attached to a bridle line or umbilical tape. A probe having a magnetic tip is used to make a connection with the magnet in the nasopharnyx. Once the connection is made, the probe is retracted out of the patient's nostril, pulling the catheter and the umbilical tape around the vomer of the patient. Caregivers have found that it is sometimes difficult to make a magnetic connection with the current magnetic bridle designs and the magnetic connection will sometimes fail during placement of the bridle.

SUMMARY

The present application discloses a bridle device and a method of placing a bridle on a person using the bridle device. In one exemplary embodiment, the bridle device comprises a retrieval portion and a delivery portion. The delivery portion has a retrieval member and a retrieval magnet attached to the retrieval member. The delivery portion has a delivery member and a delivery magnet that is movable relative to a distal portion of the delivery member. In certain embodiments, the delivery portion has a delivery tube and a delivery magnet attached to a flexible elongated member received in the delivery tube. The delivery magnet is movable relative to a distal portion of the delivery tube and both poles of the delivery magnet are exposed outside of the delivery tube.

In one exemplary embodiment, the method of placing a bridle on a person using the bridle device comprises inserting the delivery portion of the bridle device in a first nostril of the person and the retrieval portion of the bridle device in a second nostril of the person. The delivery portion comprises a delivery tube and a delivery magnet attached to a flexible elongated member received in the delivery tube. The delivery magnet is positioned outside the delivery tube and is movable relative to a distal portion of the delivery tube. The retrieval portion comprises a retrieval member and a retrieval magnet attached to the retrieval member. The delivery magnet and the retrieval magnet are connected within the nasopharynx of the person. The elongated member is pulled around the vomer bone and out the second nostril of the person by removing the retrieval member of the retrieval portion from the second nostril. The delivery tube is removed from the first nostril of the person.

In one exemplary embodiment, the bridle device comprises a retrieval portion and a delivery portion. The retrieval portion has a retrieval member and a retrieval magnet attached to the retrieval member. The delivery portion has a delivery member and a delivery magnet attached to a distal portion of the delivery member. The delivery magnet is shaped as a polyhedron. In certain embodiments, the delivery magnet is shaped as a hexahedron, cube, or rectangle.

These and additional embodiments will become apparent in the course of the following detailed description.

BRIEF DESCRIPTION OF DRAWINGS

In the accompanying drawings which are incorporated in and constitute a part of the specification, embodiments of the invention are illustrated, which, together with a general description of the invention given above, and the detailed description given below, serve to example the principles of the inventions.

FIGS. 2A-2E illustrate the attachment of various magnets to bridle lines.

FIGS. 5B and 5C are side views of the bridle device of FIG. 5A illustrating the removal of a perforation;

DETAILED DESCRIPTION OF EMBODIMENTS

Figure 1A:
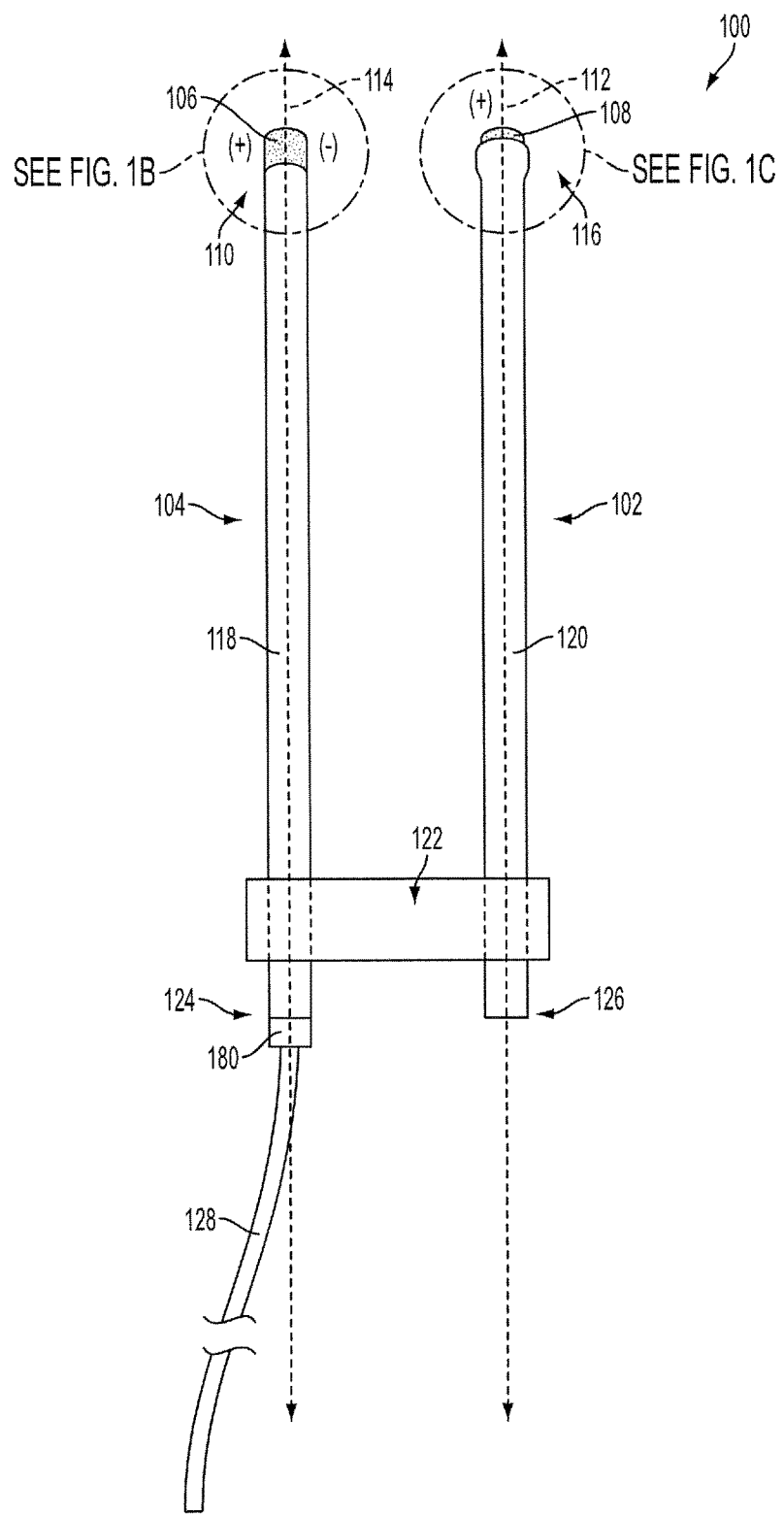
FIG. 1A is a top view of a bridle device according to an embodiment of the present application.
Figure 1B:
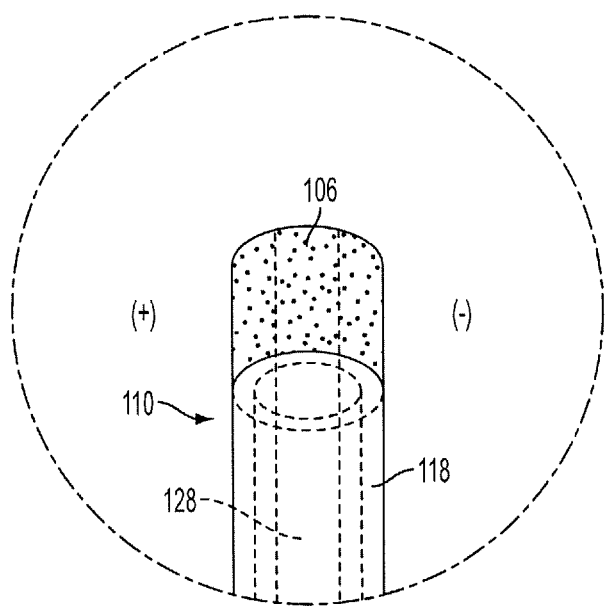
FIG. 1B is a top view of a delivery magnet of the bridle device of FIG. 1A.

The present application specification and drawings provide multiple embodiments of a bridle device. Any feature or combination of features from each of the embodiments may be used with features or combinations of features of other embodiments. As such, bridle devices in accordance with the present invention may include any combination or subcombination of the features disclosed by the present application.

Current bridle systems restrict the freedom of movement of the connecting magnets. For example, the connecting magnets are generally fixed to the catheter and probe and at least one polar surface of magnet is impaired by the body of the device. As a result, when the magnets approach one another, oriented such that as the same charged poles come into proximity of one another, the resultant repulsion impedes the establishment of a magnetic connection and/or increases placement difficulty. The presentation of same poles is problematic during lateral displacement of one or both magnets during bridle placement, which can occur in cases of both normal and abnormal anatomy, as well as inconsistencies related directly to the design and/or constitution of the bridle device itself.

The present application is directed to a bridle device and method of using a bridle device. One benefit of the bridle device is the capacity of the device to establish a magnetic connection even in circumstances where the magnets are oriented to initially repel one another. This benefit is attained by freeing at least one connecting magnet such that repulsion results in a corrective movement pattern that reorients the magnet for representation of the opposite, attractive pole resulting in the successful magnetic connection of opposite poles. Conversely, current bridle devices restrict the movement of the magnets to prohibit reorientation which often leads to bridle placement failure, difficulty, or a high level of procedural delicacy. A magnet that can reorient itself increases the probability of magnetic connection and bridle placement success. Additionally, the probability of magnetic connection success may be increased by freeing both connecting magnets to reorient themselves to present opposite poles. The probability of connection success can be further increased by selecting magnets of various shapes (similar or dissimilar) which each have free polar surfaces available for connection of both magnetic poles.

In certain embodiments discussed herein, the bridle device is described as having a delivery side and a retrieval side, or a delivery portion and a retrieval portion. For the purposes of this application, "delivery" is a modifier of those elements associated with the delivery side (which contains the bridle line) of the bridle device while "retrieval" is associated with those elements on the opposite side of the bridle device involved in puling the bridle line back out of the nose during placement. Also, the "first end" or "distal end" refers to the end of the bridle device initially entering and going into the nasal space, while "second end" or "proximal end" refers to the region farthest from the nasopharyngeal space which interacts with the user's hands.

The bridle device of the present application is generally configured to deliver a bridle line or elongated member to the nasopharyngeal space or nasopharynx of a person and wrap the bridle line around the vomer bone of the person. The bridle line generally comprises a magnet (e.g., attached to the bridle line and/or formed as part of the bridle line) that facilitates wrapping the bridle line around the vomer. The bridle line remains in the nose and wrapped around the vomer after successful bridle placement.

The bridle line may be attached to a nasal tube in order to retain and secure the nasal tube to the person. The bridle line may be attached to the nasal tube in a variety of ways, such as, for example, with a retention device (e.g., a clip or other retention mechanism) or other retention feature of the nasal tube. Co-pending U.S. patent application Ser. No. 13/839,012, filed on Mar. 15, 2013 and titled "Nasal Tube Device and Method", discloses various nasal tubes and retention features. Any feature or combination of features of the nasal tubes and/or retention features disclosed in U.S. patent application Ser. No. 13/839,012 may be used with features or combinations of features of the bridle device embodiments of the present application. As such, bridle devices in accordance with the present invention may include any combination or subcombination of the features of the nasal tubes and/or retention features disclosed in U.S. patent application Ser. No. 13/839,012.

FIGS. 1A-1E illustrate an exemplary embodiment of a bridle device 100 according to an embodiment of the present application. The bridle device 100 comprises a retrieval portion 102 and a delivery portion 104. The retrieval portion 102 comprises a retrieval magnet 108 attached to a distal portion 116 of a retrieval arm or member 120. The delivery portion 104 comprises a delivery tube 118 and a delivery magnet 106 that is movable relative to a distal portion 110 of the delivery tube 118. The delivery magnet 106 is attached to a bridle line 128 that is received in the delivery tube 118. As shown, the bridle line 128 is a flexible elongated member and the delivery magnet 106 is positioned outside the delivery tube 118 and is movable relative to the distal end of the delivery tube 118. Both poles (+ and −) of the delivery magnet 106 are exposed outside of the delivery tube 118 such that the delivery magnet may orient itself within the nasopharyngeal space to connect with the retrieval magnet 108. In certain embodiments, the delivery magnet 106 is rotatable relative to the distal end of the delivery tube 118 and about a longitudinal axis 114 of the delivery tube.

Figure 1C:
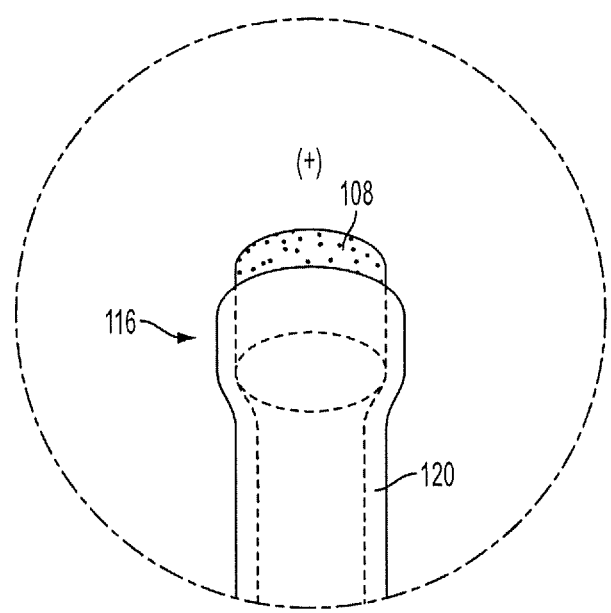
FIG. 1C is a top view of a retrieval magnet of the bridle device of FIG. 1A.
Figure 1D:
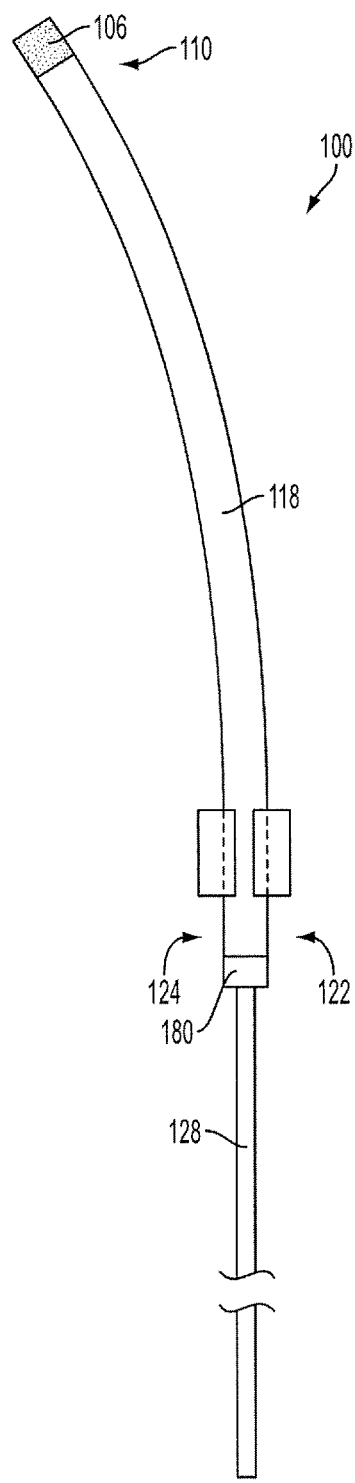
FIG. 1D is a side view of the bridle device of FIG. 1A.
Figure 1E:
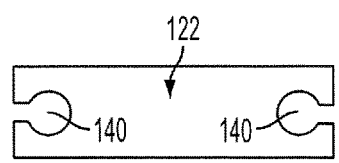
FIG. 1E is a front view of a handle of the bridle device of FIG. 1A.
Figure 1F:
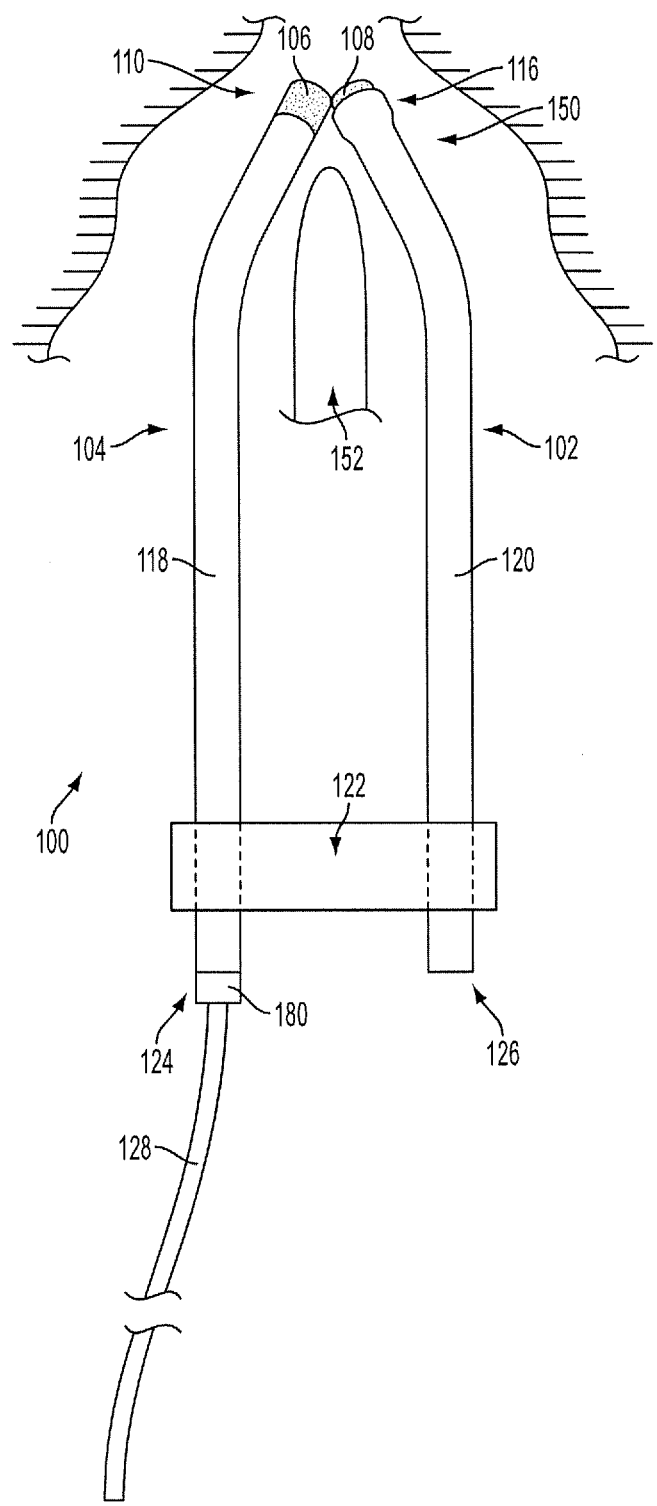
FIGS. 1F-1H are top views illustrating the placement of a bridle line using the bridle device of FIG. 1A.
Figure 1G:
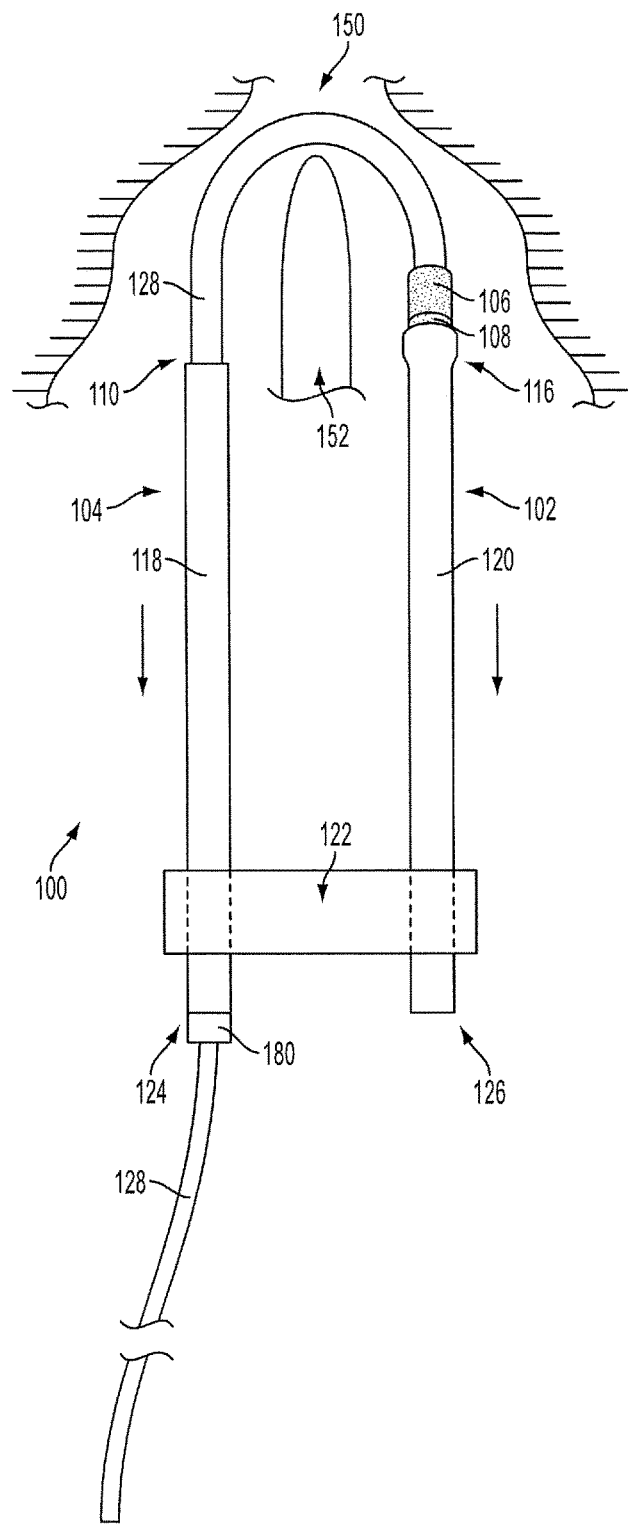
Figure 1H:
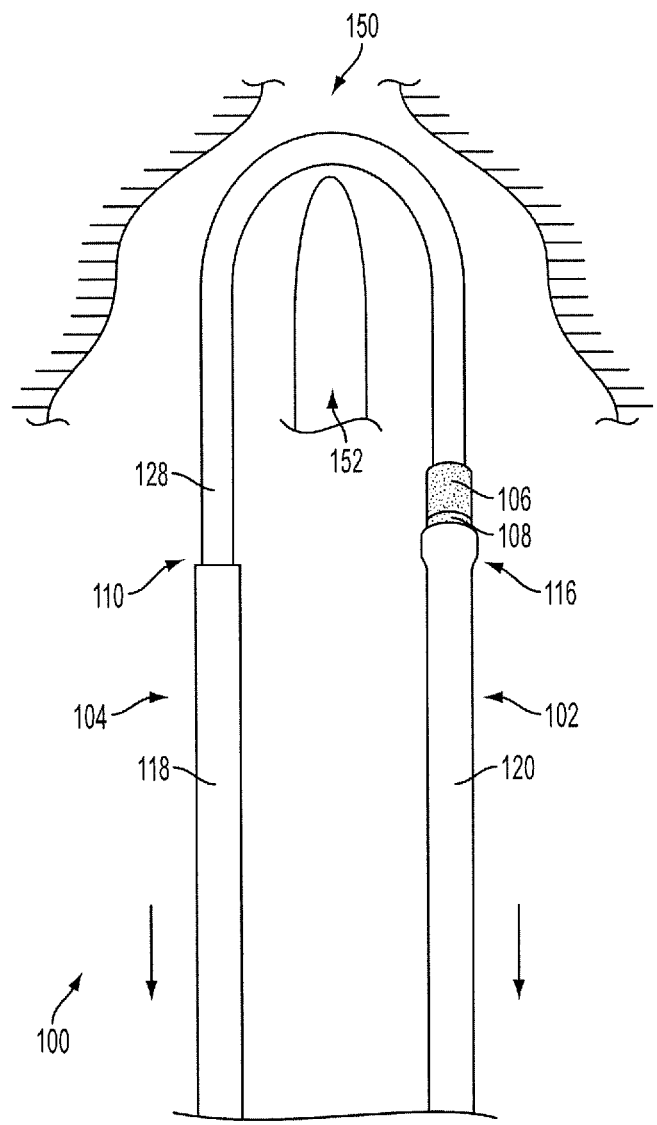

FIGS. 1F-1H illustrate an exemplary method of placing the bridle device 100 on a person. The delivery tube 118 of the delivery portion 104 is inserted into a first nostril of a person and the delivery magnet 106 is positioned in the nasopharynx 150 of the person. The retrieval member 120 of the retrieval portion 102 is inserted into a second nostril of the person and the retrieval magnet 108 is positioned in the nasopharynx 150 of the person. As illustrated in FIG. 1F, the delivery magnet 106 and the retrieval magnet 108 form a magnetic connection in the nasopharynx 150 of the person. As stated above, the delivery magnet 106 is movable relative to the distal end of the delivery tube 118 and both poles (+ and −) of the delivery magnet are exposed outside of the delivery tube such that the delivery magnet may orient itself within the nasopharyngeal space 150 to connect with the retrieval magnet 108. As illustrated in FIGS. 1G and 1H, the delivery tube 118 and the retrieval member 120 are then retracted out of the nasopharynx 150, pulling the bridle line 128 around the vomer bone 152 of the person. The bridle line 128 is also pulled out the second nostril of the person by removing the retrieval member 120 from the second nostril. The delivery tube 118 is removed from the first nostril of the person. The delivery tube 118 slides over the bridle line 128 as the delivery tube is removed from the first nostril.

The delivery magnet of the bridle device may be attached to the bridle line in a variety of different ways such that the delivery magnet is permitted to move relative to the distal portion of the delivery tube. For example, as illustrated in FIGS. 2A-2E, a delivery magnet 206 may be attached directly to a bridle line 228, such as with an adhesive (see FIG. 2A), knot 270 (see FIG. 2B), eyelet 274 (see FIG. 2D), or any other fastener that attaches the delivery magnet to the bridle line and permits the delivery magnet to move relative to the distal portion of the delivery tube.

In certain embodiments, the bridle line may be attached to the delivery magnet by a delivery adapter. The delivery adapter may be configured in a variety of ways to facilitate passage of the delivery magnet into the nasopharyngeal space and/or connection of the delivery magnet to the retrieval magnet. For example, as illustrated in FIG. 2E, the delivery adapter may be a housing 276 that retains the delivery magnet 206 and anchors the bridle line 228. Further, as illustrated in FIG. 2C, the delivery adapter may be a low profile sheath or pouch 272 that wraps around and retains the delivery magnet 206. As shown, the bridle line 228 forms the sheath or pouch 272 that houses the delivery magnet 206.

In certain embodiments, the delivery magnet may be partially encased or fully encased (i.e., completely surrounded on all sides) in the delivery adapter. For example, the delivery magnet may be incorporated into a silicone delivery adapter that encases the magnet. In certain embodiments, the delivery magnet is shaped as a cylinder with opposite poles located at each end and is encased in a delivery adapter that orients the delivery magnet so that the poles of the delivery magnet are free and exposed. Further, the delivery adapter may comprise a tapered end (see, e.g., housing 276 in FIG. 2E) and includes an opening to receive and retain the bridle line.

Figure 3A:
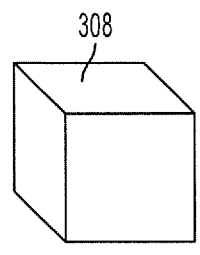
FIGS. 3A-3E illustrate various magnet shapes.
Figure 3B:
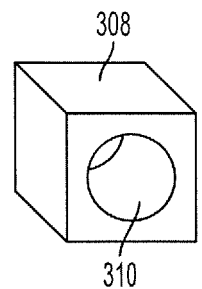
Figure 3C:
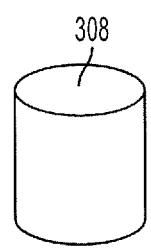
Figure 3D:
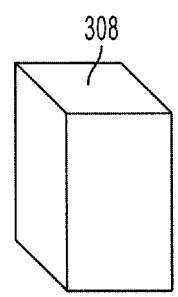
Figure 3E:
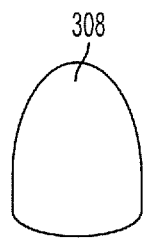

The delivery magnet may be a variety of different shapes and sizes. For example, as illustrated in FIGS. 3A-3E, the delivery magnet 308 may be shaped as a cube (see FIGS. 3A and 3B), rectangle (see FIG. 3D), cylinder (see FIG. 3C), dome (see FIG. 3E), capsule, tablet, sphere, or about any other shape that facilitates passage of the delivery magnet into the nasopharyngeal space and connection of the delivery magnet to the retrieval magnet. Further, as illustrated in FIG. 3B, the delivery magnet 308 may comprise an opening 310, for example, to attach the magnet to a fastener, eyelet, bridle line, or the like.

Many of the embodiments shown in the Figures of the present application comprise a cylindrical magnet where the magnetic poles are located on the external surface of the cylinder tangent to the longitudinal axis of the cylinder (see, e.g., FIGS. 1A and 2A-2E). However, it should be understood that the bridle device of the present application may comprise a variety different sizes and shapes of magnets. For example, magnets in the shape of a polyhedron, such as a hexahedron (e.g., the cube shown in FIGS. 3A and 3B or rectangle shown in FIG. 3D), may have a similar diameter to the cylindrical magnets and similar magnetic attraction forces. However, a polyhedron magnet may be smaller than the cylindrical magnet and better suited for maneuverability in the anatomical spaces in which it would function. Additionally, a polyhedron magnet may not create the same torque over its length relative to a cylindrical magnet and therefore, demonstrate less propensity for disconnection resulting from torque forces. For example, in certain embodiments, the delivery magnet of the bridle device of the present application is shaped as a hexahedron (e.g., the cube shown in FIGS. 3A and 3B or rectangle shown in FIG. 3D) and the reduced torque, difference in surface area and length of the magnet relative to cylindrical magnets permits the bridle to make tighter turns around the vomer bone than cylindrical magnets, especially for smaller patients.

The delivery magnet is also sized to permit passage of the magnet through the nostrils and into the nasopharyngeal space of the person. The delivery magnet is generally between about 1 mm and about 5 mm in diameter (or width or height) and between about 1 mm and about 7 mm in length. In certain embodiments, the delivery magnet is cylindrical in shape, about 2.5 mm in diameter and about 5 mm in length. In another embodiment, the delivery magnet is cubic in shape and between about 1 mm and about 3 mm in length, width, and height.

Figure 7A:
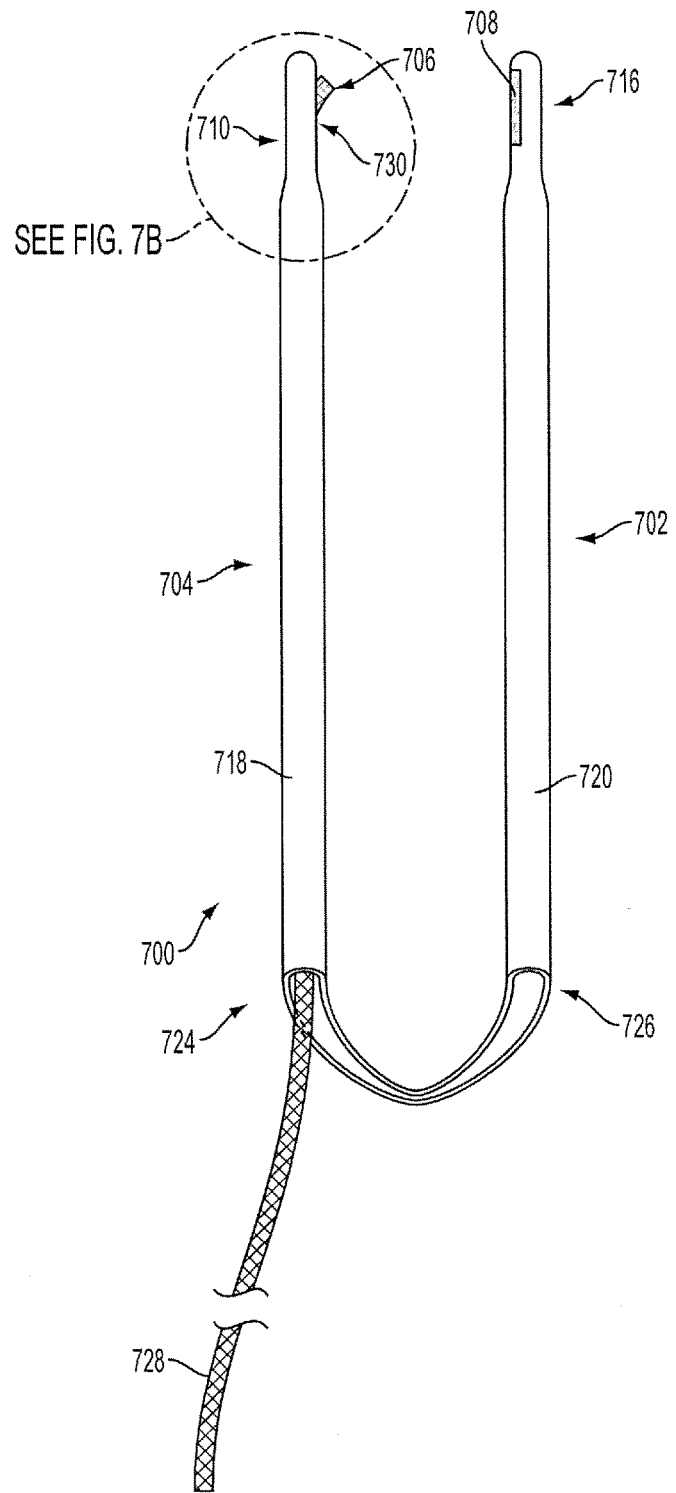
FIG. 7A is a top view of a bridle device according to an embodiment of the present application.
Figure 7B:
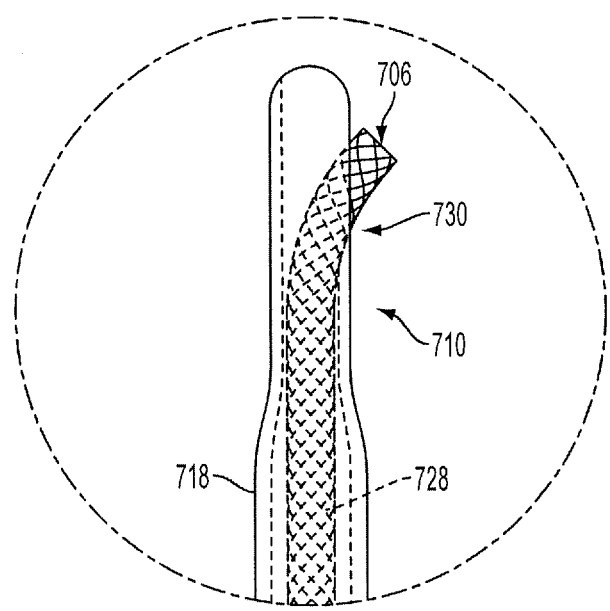
FIG. 7B is a top view of a delivery magnet of the bridle device of FIG. 7A.
Figure 7C:
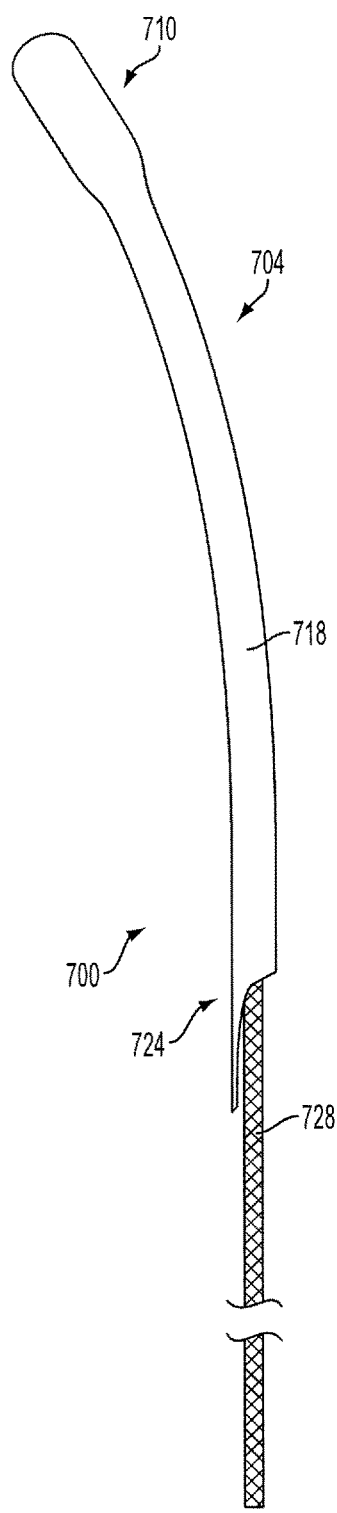
FIG. 7C is a side view of the bridle device of FIG. 7A.

The bridle line may also be configured such that it forms the delivery magnet or a portion thereof. For example, FIGS. 7A-7C illustrate a bridle device 700 according to an embodiment of the present application wherein at least a portion of the bridle line 728 is magnetic. As shown, the bridle line 728 of the bridle device 700 is a flexible elongated member having a woven structure. The bridle line 728 comprises magnetic fibers (e.g., metallic or iron based fibers) capable of being magnetically connected to the retrieval magnet 708. The entire bridle line 728 or only a portion of the bridle line (e.g., only the distal portion 706 of the bridle line) may comprise magnetic fibers to make the bridle line magnetic. The magnetic bridle line 728 generally comprises a larger surface area than other magnet shapes to facilitate connection to the retrieval magnet 708. Further, as shown in FIGS. 7A and 7B, the retrieval magnet 708 also comprises a larger surface area than other magnet shapes to facilitate connection to the magnetic bridle line 728. The bridle line of the present application (or a magnetic region of the bridle line) may be treated, impregnated, laminated, or used in conjunction with a delivery adapter to control the stiffness and/or direction of the bridle line or the magnetic region.

The shape of the delivery and retrieval magnets of the bridle device may also be dissimilar to enhance the connection process. The strength of the magnetic connection between the delivery and retrieval magnets is relevant for generating a sufficient attractive force to establish a connection and maintaining sufficient attractive force during retrieval to prevent disconnection. The dissimilar delivery and retrieval magnets may be utilized to create a lock-and-key scenario in which a magnetic connection is reinforced by mechanical interference. For example, a ball magnet may interact with disk or a partially hollowed cylinder such that the ball fits into the disk void to create a lock-and-key interaction with both magnetic and mechanical retention capabilities.

In certain embodiments, the delivery magnet may be configured such that it is disposed at the distal end of the delivery tube (i.e., the end of the tube that initially enters the nostril of the person). For example, the delivery magnet may be configured such that the diameter of the magnet (or the diameter of the delivery adapter) is slightly larger than the distal end of the delivery tube. As such, the delivery magnet is disposed on the distal end of the delivery tube, or sits on the distal end, during insertion of delivery tube into the nostrils of the person. Further, in certain embodiments, at least a portion of the delivery magnet (or the delivery adapter) may be at least partially received in a bore, lumen or channel at the distal end of the delivery tube to facilitate insertion of delivery magnet into the nasopharyngeal space of the person (e.g., reduced overall profile) and protect the magnet from dislodgement during placement.

For example, a portion of the delivery magnet and/or delivery adapter may be configured such that the diameter of the portion is less than the interior diameter of the distal end of the delivery tube lumen. As such, the portion of the delivery magnet or adapter having the reduced diameter may be received in the distal end of the delivery tube. In certain embodiments, the delivery magnet is encased in a delivery adapter that comprises a tapered portion that may be received in the distal end of the delivery tube (see, e.g., tapered portion of housing 276 in FIG. 2E). Further, a portion of the delivery adapter may be cone shaped and partially fits into the distal end of the delivery tube lumen until the diameter of the delivery adapter is greater than the lumen. The delivery magnet may also comprise a tapered portion or cone shaped portion such that may be received in the distal end of the delivery tube.

In certain embodiments, the distal end of the delivery tube may comprise a device configured to assist with deployment of the delivery magnet. The magnet deployment device may comprise, for example, a spring or additional magnet that creates space between the delivery magnet (or the delivery adapter) and the distal end of the delivery tube during placement of the bridle. The magnet deployment device may also comprise a feature or element that creates magnetic repulsion in the distal portion of the delivery tube or increases the air pressure behind the delivery magnet to deploy the magnet. By creating space between the delivery tube and the delivery magnet, the delivery magnet will have increased maneuverability in the nasopharyngeal space in which to execute its corrective movements. The magnet deployment device may also be used to move or force a delivery magnet that is partially or completely received in the delivery tube lumen out the distal end of the lumen. Space may also be created between the delivery magnet (or the delivery adapter) and the distal end of the delivery tube by retreating the delivery tube and/or due to the magnetic interaction between the delivery and retrieval magnets.

The bridle device of the present application may also comprise a delivery stop or anchor that holds and maintains tension on the bridle line received in the delivery tube as the delivery tube is inserted into the nose of the person. For example, as illustrated in FIGS. 1A, 1D, 1F and 1G, the bridle line 128 is removably attached to a delivery stop 180 at the proximal portion 124 or proximal end of the delivery tube 118 such that tension is maintained on the bridle line. The delivery magnet 106 disposed at the distal end of the delivery tube 118 does not pull through the delivery tube when the bridle line 128 is tensioned. As illustrated in FIGS. 1A, 1D, 1F, under tension, the delivery magnet 106 and delivery tube 118 effectively function as a single unified delivery member, so that, for example, the magnet will rotate as the delivery tube is rotated and will advance/retreat as the delivery tube is advanced/retreated. The delivery tube 118 and delivery magnet 106 are inserted into the nose and advanced to position the delivery magnet to the nasopharnyx. As illustrated in FIG. 1G, once in the nasopharyngeal space, the bridle line 128 is removed from the delivery stop 180 and tension on the bridle line is relieved. As such, the delivery magnet 106 is movable relative to the distal end of the delivery tube 118 and the bridle line 128 is movable relative to the delivery tube. Further, the untensioned delivery magnet 106 may also move away from the distal end of the delivery tube 118 and/or experience the recoil of the bridle line due to its elasticity thereby creating space between the delivery magnet (or the delivery adapter) and the distal end of the delivery tube. The delivery stop 180 may be a variety of components capable of maintaining tension on the bridle line and permitting removal of the bridle line, such as, for example, a post, clip, cleat, fastener, notch, opening, anchor, restrictor, or the like disposed in and/or extending from the bridle device (e.g., the delivery tube of the bridle device).

The bridle line of the present application may comprise a wide range of flexible, biocompatible materials that are strong enough to secure a nasal tube to a person, such as, for example, a fiber reinforced polymeric material, woven textile, and/or braided strands. In certain embodiments, the bridle line comprises a fiber reinforced polymeric material such as polyurethane impregnated nylon. The polyurethane platform is biocompatible, versatile, flexible, and interacts well with other materials. A polyurethane bridle line is also light, has a low coefficient of friction on mucosal surfaces, does not absorb fluid, and can act as a platform for surface treatments for various purposes. Decreased friction of the bridle line during retrieval minimizes mucosal trauma and reduces the magnitude of magnetic strength required during retrieval. A polyurethane bridle line also possesses strong material characteristics for both short term and longer term retention in the nasal mucosa. The nylon fibers act to provide strength and control the elasticity of the polyurethane; in particular, the nylon fibers can control elongation to preserve the width (or diameter if the bridle line is a tube) under bridle line tension. A nylon impregnated, polyurethane bridle line also demonstrates strong self-bonding characteristics when heated which is a primary manufacturing mechanism by which to attach the bridle line to a delivery adapter without the use of adhesives, extra components, or other materials or processes.

The delivery tube generally possesses some flexibility to deliver the magnet through a nostril and into the nasopharyngeal space of the person. However, the delivery tube also possesses sufficient column strength to advance through the nasal passage. Further, the delivery tube is generally not pulled around the internal nasal septum during retrieval and therefore, its construction is not limited by the requirement that it must be flexible enough to be bent around the septum. The delivery tube may have one or more bends along its length (not necessarily straight) and may be tapered or regionally non-uniform in diameter. Bends may accommodate anatomy for placement ease and when rotated, bring the magnet closer to the internal nasal midline to find the retrieval magnet as well as change the orientation of the delivery magnet as the delivery arm is rotated.

The delivery tube of the present application may comprise a wide range of biocompatible materials that are strong enough to deliver a magnet through a nostril and into the nasopharyngeal space of a person, such as, for example, polytetrafluoroethylene (PTFE), polyurethane, PVC, polypropylene, elastomers, and thermoplastics generally lend themselves well to this application. Further, the delivery tube may also comprise one or more internal reinforcement strands and/or coils to achieve a more compliant tissue/tube interface while maintaining column strength and tube integrity during placement (e.g., to reinforce a softer tube material). In certain embodiments, a PTFE catheter was used as the delivery tube for its low frictional resistance. Current bridle devices have a higher frictional resistance, require a stylet for rigidity, and demonstrate decreased performance relative to the bridle device of the present application. Additionally, an transparent delivery tube which allows for a view of the bridle line as it passes through the delivery tube aids in recognition of a magnetic connection between the delivery magnet and the retrieval magnet. For example, the bridle line can be seen to move within the delivery tube in response to the retrieval portion after a connection has been made. Further, the bridle line may comprise a visual indicator, such as, for example, demarcations or colored portions, to facilitate visualization of the bridle line's movement.

Figure 5A:
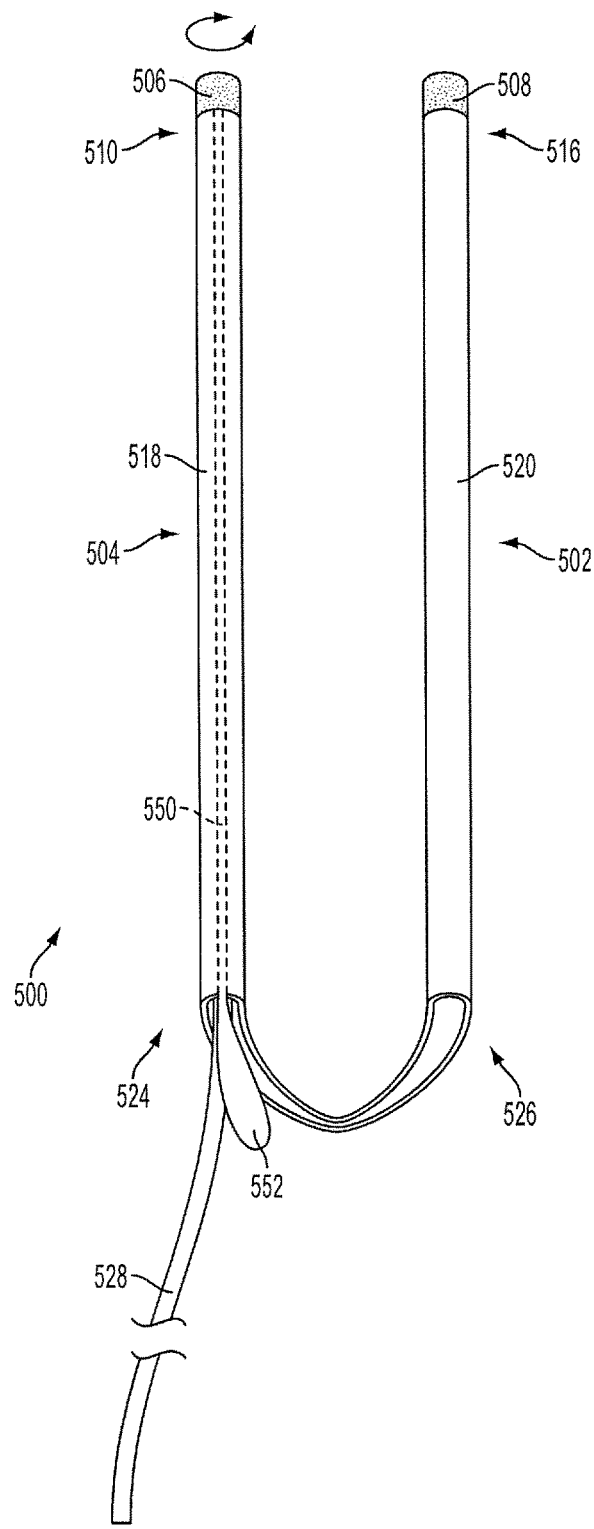
FIG. 5A is a top view of a bridle device according to an embodiment of the present application.

FIGS. 5A-5C illustrate another exemplary embodiment of a bridle device 500 according to an embodiment of the present application. The bridle device 500 comprises a retrieval portion 502 and a delivery portion 504. The retrieval portion 502 has a proximal portion 526 and a distal portion 516, and the delivery portion 504 has a proximal portion 524 and a distal portion 510. The retrieval portion 502 comprises a retrieval magnet 508 attached to the distal portion 516 of a retrieval arm or member 520. The delivery portion 504 comprises a delivery tube 518 and a delivery magnet 506 that is movable relative to the distal portion 510 of the delivery tube 518. The delivery magnet 506 is attached to a bridle line 528 that is received in the delivery tube 518. As shown, the bridle line 528 is a flexible elongated member and the delivery magnet 506 is positioned outside the delivery tube 518 and is movable relative to the distal end of the delivery tube 518.

Figure 6A:
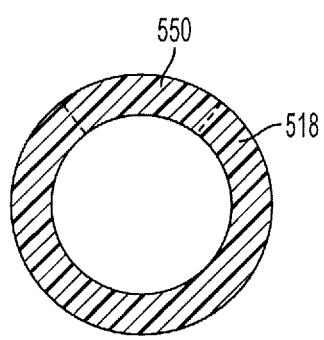
FIGS. 6A-6D are cross sectional views of various delivery tubes according to embodiments of the present application.
Figure 6B:
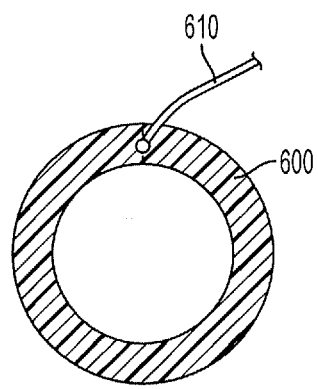
Figure 6C:
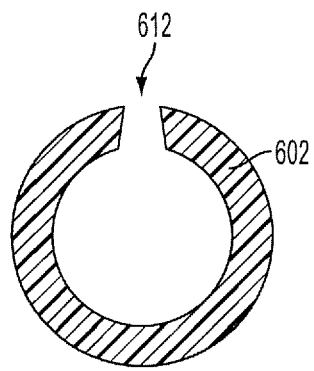
Figure 6D:
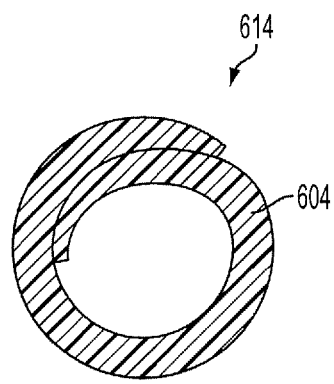

As discussed above, the bridle line may be removed from the bridle device by sliding it through and out the distal end of the delivery tube during retrieval of the delivery tube from the nasopharynx of the person. However, in certain embodiments, the wall of the delivery tube may be separated substantially along its length such that the bridle line may be separated from the delivery tube without having to slide the bridle line through the delivery tube and out its distal end. As such, the bridle line may be removed from the delivery tube when the delivery tube is attached to a nasal tube (e.g., a nasopharyngeal airway) or other device. In this regard, the nasal tube or other device may be attached to the bridle line prior to placement of the bridle on the person. For example, FIG. 6C illustrates the cross section of a delivery tube 602 having a longitudinal cut or slit 612 that permits removal of the bridle line from the delivery tube. FIG. 6D illustrates a wrapped delivery tube 604 having overlapping walls 614 that permit the bridle line to be removed from the delivery tube. In certain embodiments, the delivery tube may comprise a slit or slot at approximately 12 o'clock on the cross section and a stop at approximately 6 o'clock on the cross section.

Further, in certain embodiments, the delivery tube may comprise one or more perforated sections and/or perforations that may be removed to separate the delivery tube wall. For example, FIGS. 5A-6A illustrate the bridle device 500 comprising a delivery tube 518 having a perforated section 550. As shown in FIGS. 5B and 5C, the perforated section 550 may be removed and the delivery tube walls separated by pulling on the pull tab 552. The perforated section 550 may be removed the entire length of the delivery tube 518 from the proximal portion 524 to the distal portion 510 of the delivery tube. FIG. 6A illustrates a cross sectional view of the delivery tube 518 showing the removable perforated section 550. FIG. 6B illustrates a cross sectional view of a delivery tube 600 having a single perforation with an impregnated string 610. Pulling the string 610 separates the delivery tube wall.

In the embodiments herein, the delivery portion of the bridle device is described and shown as having a delivery tube and a bridle line received within the delivery tube. However, it should be understood that the bridle device of the present application may comprise a delivery member or delivery arm that is not formed as a tube having a lumen or channel for the bridle line.

For example, the bridle device may comprise a flexible delivery member having a delivery magnet at its distal end that is configured to move relative to the delivery member (e.g., attached to the distal end by a flexible elongated member, movably attached to the distal end of the delivery member, or the like). Further, the delivery magnet may be configured such that at least a portion of the magnet (or delivery adapter) is received in a distal end of the delivery member (e.g., in a bore or channel of the delivery member).

The delivery member may be attached to a bridle line and, once the delivery magnet connects with the retrieval magnet, the delivery member and the bridle line are pulled around the vomer bone of the person.

In certain embodiments, the delivery magnet may be attached to the delivery member such that the delivery magnet is movable relative to the delivery member. For example, the region between the delivery magnet and the delivery member and/or just below the delivery magnet may comprise a flexible material that permits the magnet to move relative to the delivery member. In certain embodiments, the delivery magnet is attached to the delivery member with one or more pieces of flexible heat shrink tubing that permits the magnet to move relative to the delivery member. Further, in other embodiments, the delivery member may comprise one or more regions having different thicknesses such that the delivery magnet is movable relative to the delivery member (e.g., a thinner distal portion attached to the delivery magnet).

In certain embodiments, the delivery magnet may be removable from the delivery member and connected to a bridle line that is wrapped around the vomer bone of the person. The bridle line may also engage the delivery member such that it can be removed from the delivery member when the delivery magnet connects with the retrieval magnet in the nasopharynx. For example, the bridle line may be: wrapped around a portion of the delivery member; removably attached to the delivery member by a post, clip, cleat, fastener, notch, opening, anchor, or the like; or disposed in a groove or channel of the delivery member.

As discussed above, the retrieval member of the retrieval portion may be inserted into the opposite nostril and advanced until the distal end of the retrieval member reaches the nasopharyngeal space. The retrieval member is generally inserted concurrently or just prior to insertion of the delivery tube and the delivery magnet. The retrieval member may be solid or hollow and is generally flexible and accommodating to the nasal mucosa but retains sufficient column strength for insertion and retrieval. The retrieval member may have one or more bends or curves to mimic the anatomical pathways of the person as well as increase the probability of establishing a magnetic connection with the delivery magnet of the delivery portion. Once the retrieval member and delivery tube are both positioned in the nasaopharyngeal space, the retrieval member (as well as the delivery tube) may be rotated or twisted to encourage the establishment of a magnetic connection. Twisting the retrieval member and the delivery tube will alter the distance between the retrieval and delivery magnets, as well as alter the orientation of the two magnets which aids in overcoming repulsion.

The retrieval magnet of the retrieval portion may be shaped and sized as discussed above with reference to the delivery magnet. The retrieval magnet may be similar or dissimilar in size and/or shape to the delivery magnet. Further, the retrieval magnet may be fixed or free relative to the retrieval member. For example, as illustrated in FIGS. 1A and 1C, the retrieval magnet 108 is cylindrical in shape and is fixed to the distal portion 116 of the retrieval member 120. As shown, the positive pole of the retrieval magnet 108 is exposed and the negative pole is buried in the retrieval member 120. However, in certain embodiments, the retrieval magnet may be fixed to the distal portion of the retrieval member such that both the positive and negative magnetic poles are exposed to increase the opportunity for a magnetic connection with the delivery magnet.

The retrieval portion of the bridle device may be configured such that the retrieval magnet is movable relative to a distal portion of the retrieval member. For example, the retrieval member may "freely" retain the retrieval magnet so as to allow a degree of correctional movements similar to, if not the same as, the delivery magnet and further increase the ease and likelihood of a magnetic connection between the magnets. As such, the retrieval member and the retrieval magnet of the bridle device may be configured in any of the ways described herein that permit the delivery magnet to move relative to the delivery tube or the delivery member.

For example, FIGS. 4A-4D illustrate a bridle device 400 according to an embodiment of the present application. As shown, the delivery portion 404 comprises a delivery tube 418 and a delivery magnet 406 that is movable relative to a distal portion 410 of the delivery tube. The delivery magnet 406 is attached to a bridle line 428 that is received in the delivery tube 418. As shown, the bridle line 428 is a flexible elongated member and the delivery magnet 406 is positioned outside the delivery tube 418 and is movable relative to the distal end of the delivery tube. Both poles (+ and −) of the delivery magnet 406 are exposed outside of the delivery tube 418 such that the delivery magnet may orient itself within the nasopharyngeal space to connect with the retrieval magnet 408. The delivery magnet 406 is rotatable relative to the distal end of the delivery tube 418 and about a longitudinal axis 414 of the delivery tube.

As illustrated in FIGS. 4A-4D, the retrieval portion 402 of the bridle device 400 comprises a retrieval member 420 formed as a retrieval tube and a retrieval magnet 408 that is movable relative to a distal portion 416 of the retrieval tube. Similar to the delivery magnet 406, the retrieval magnet 408 is attached to a flexible elongated member 430, is positioned outside the retrieval tube 420 and is movable relative to the distal end of the retrieval tube. Both poles (+ and −) of the retrieval magnet 408 are exposed outside of the retrieval tube 420 such that the retrieval magnet may orient itself within the nasopharyngeal space to connect with the delivery magnet 406. The retrieval magnet 408 is rotatable relative to the distal end of the retrieval tube 420 and about a longitudinal axis 412 of the retrieval tube.

As illustrated in FIGS. 4A-4D, the flexible elongated member 430 of the retrieval portion 402 is knotted 432 outside the proximal portion 426 of the retrieval tube 420 to attach the retrieval magnet 408 to the retrieval tube while still permitting the magnet to move relative to the tube. However, in other embodiments, the retrieval magnet may be directly attached to the retrieval member (e.g., to a distal portion or distal end of the member) such that it is movable relative to the retrieval member (e.g., attached to the distal end by a flexible elongated member, rotatably attached to the distal end, or the like).

As illustrated in FIGS. 4A-4D, the flexible elongated members 428, 430 attached to the delivery and retrieval magnets 406, 408, respectively, is a woven tubular structure similar to a hosiery sock. Each magnet 406, 408 is retained inside one end of the pouch or sheath 440, 442 formed by the flexible elongated member 428, 430 and remains free to rotate and orient itself. However, it should be understood that the delivery magnet 406 and/or the retrieval magnet 408 may be attached to the flexible elongated member 428, 430 by any of the methods described herein.

The delivery portion may be connected to the retrieval portion of the bridle device. As such, the delivery tube and the retrieval member may be held in position during advancement and placement of the bridle device, e.g., substantially parallel and equidistant to each other. Further, the delivery portion and the retrieval portion may be simultaneously inserted and/or removed from the nasopharyngeal space of the person.

For example, as illustrated in FIGS. 1A, 1D and 1E, the delivery tube 118 and the retrieval member 120 of the bridle device 100 are connected together by a handle 122 having open channels 140 configured to receive the delivery tube and the retrieval member. As shown, the open channels 140 are sized and shaped to form a friction or interference fit with the delivery tube 118 and the retrieval member 120.

Figure 4A:
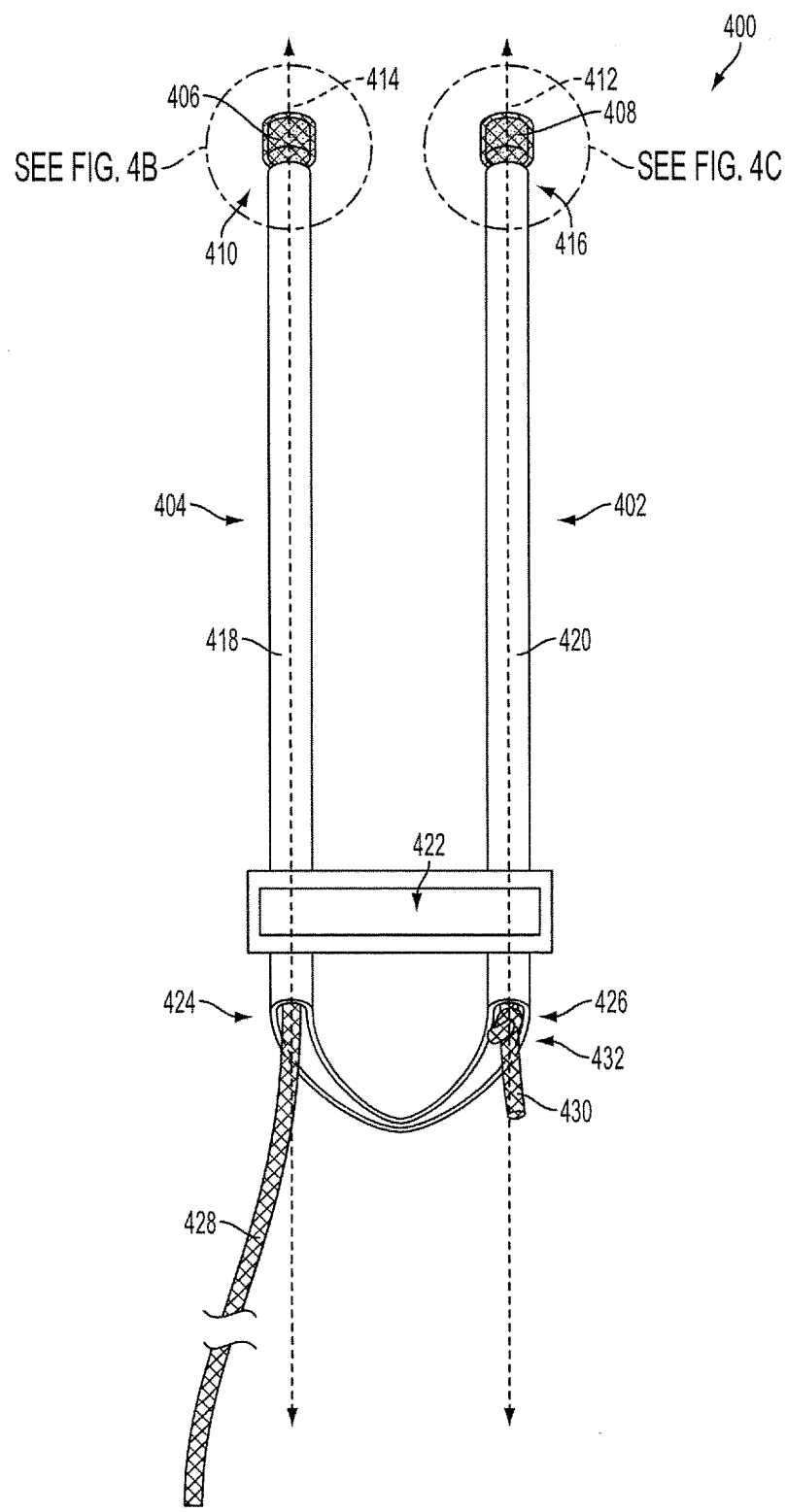
FIG. 4A is a top view of a bridle device according to an embodiment of the present application.
Figure 4B:
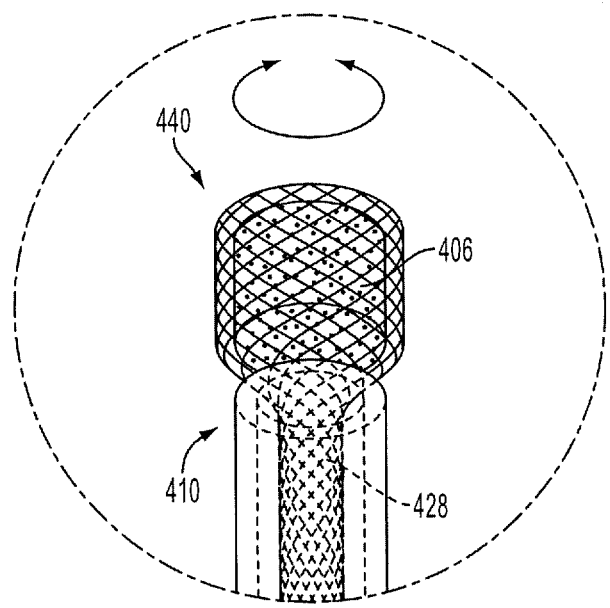
FIG. 4B is a top view of a delivery magnet of the bridle device of FIG. 4A.
Figure 4C:
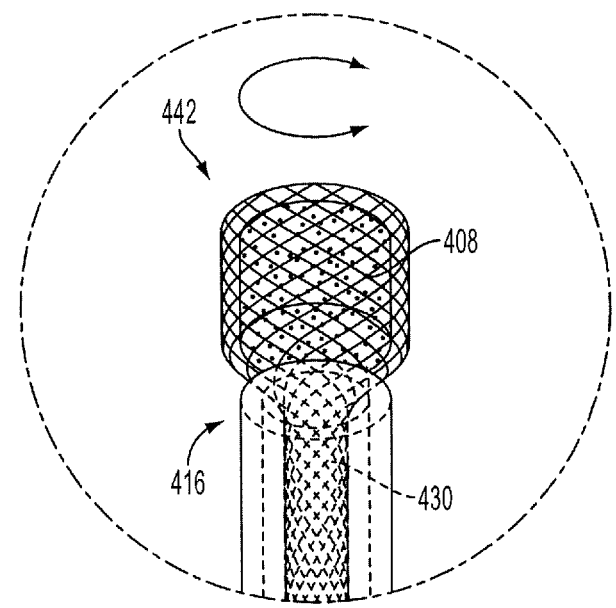
FIG. 4C is a top view of a retrieval magnet of the bridle device of FIG. 4A.
Figure 4D:
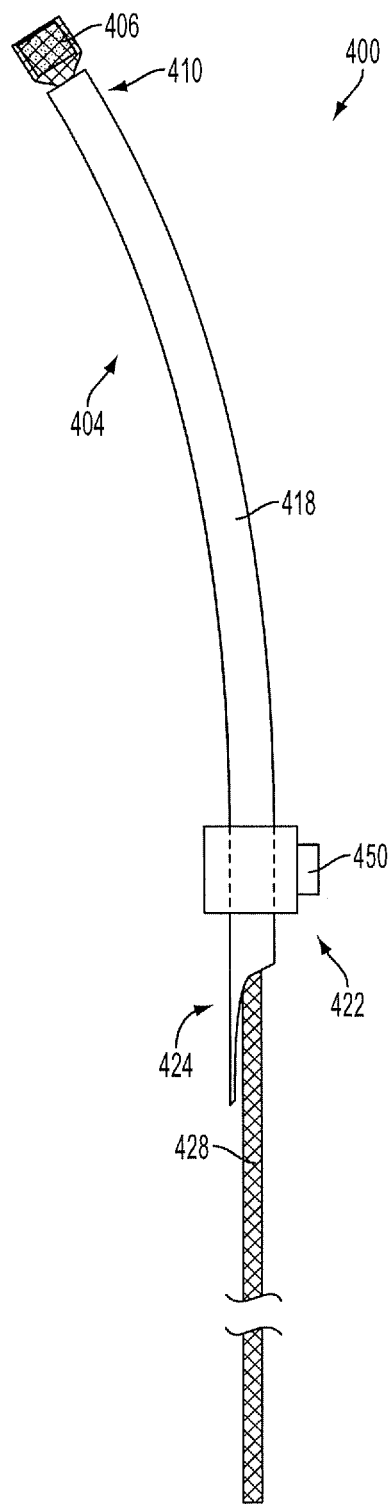
FIG. 4D is a side view of the bridle device of FIG. 4A.
Figure 4E:
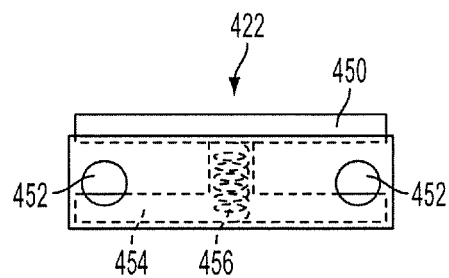
FIG. 4E is a front view of a handle of the bridle device of FIG. 4A.

As illustrated in FIGS. 4A, 4D and 4E, the delivery tube 418 and the retrieval tube 420 of the bridle device 400 are connected together by a clamping handle 422 having channels 452 configured to receive the delivery tube and the retrieval tube. As shown, pressing down on the button 450 releases the clamp 454 that is pressed against the delivery and retrieval tubes 418, 420 so that they may slide through the channels 452 of the clamping handle 422. Further, releasing the button 450 allows the spring 456 to close the clamp 454 on the delivery and retrieval tubes 418, 420. In certain embodiments, the clamping handle 422 may also be used to clip or cut one or both of the delivery and retrieval tubes 418, 420.

The handle of the bridle device (e.g., handle 122 and 422) may also be used to secure one or both ends of the bridle line. For example, after the bridle line has been placed around the vomer bone of the person, the handle may slide up toward the nose of the person and function as a clamp or external retention mechanism for one or both ends of the bridle lines.

In certain embodiments, the delivery tube and the retrieval member or tube are formed as a unitary component. For example, the bridle devices illustrated in FIGS. 4A-5C and 7A-8D are formed from a single U-shaped piece or "wishbone" shaped piece. The retrieval member or tube forms a first side of the U and the delivery tube forms a second side of the U. Further, the proximal portions of the delivery tube and the retrieval member or tube are joined together to form the U-shaped piece. All of the aforementioned features of magnetic correction may be utilized in these wishbone embodiments.

There exists multiple advantages of the wishbone embodiments over traditional two-part bridle systems. First, the wishbone embodiment requires one hand for placement rather than two hands, which provides numerous advantages, especially in emergency scenarios. Second, connecting the delivery and retrieval tubes permit advancement of each side's respective magnet through the nasal cavities and into the nasopharyngeal space at the same rate, distance and level. This method of deployment increases the probability of establishing a magnetic connection because the distance each arm travels is sure to be the same. In traditional two part bridle systems, it is difficult to know just how far one side has advanced relative to the other side and if the two sides are not generally advanced equally, establishing a magnetic connection may be difficult. Further, the control of rate and distance helps the caregiver to deploy the wishbone along the same general path intranasally. In other words, even in normal anatomy of a single individual, each nasal cavity demonstrates its own unique variable anatomy. Even in a single nasal cavity, the anatomy is not uniform superior to inferior, medial to lateral. In a traditional two-part bridle system, this anatomical variability contributes to difficulty establishing a magnetic connection by altering the path each bridle side takes through the course of the nasal passageways ultimately delivering the second ends to the pharyngeal space with are too far apart for a magnetic connection.

Preferably, the bridle is placed on each side by advancing the magnets along the floor of the respective nasal cavities, inferior to the inferior nasal turbinate and at equal distances behind the posterior free edge of the vomer, however, ideal placement may be difficult to achieve consistently across patients. The wishbone embodiment aids in controlling spacing, delivery rate, and nasal pathway which contributes to overcoming the difficulties posed by variable nasal anatomy resulting in failed or difficult magnetic connections. This embodiment also allows for simultaneous placement and retrieval with one movement.

The delivery tube and the retrieval member or tube of the bridle device may be shaped and configured in a variety of ways to facilitate placement and connection of the delivery and retrieval magnets. For example, the morphology of the delivery tube and/or the retrieval member or tube may ease travel of the tube or member through the nasal passage of the person. In this regard, the tube or member may be formed and/or sized such that the tube or member overcomes resistance and obstacles through the nasal passage travel path to increase patient comfort and reduce tissue trauma.

For example, FIGS. 7A-7C illustrate a bridle device 700 comprising a spatula shaped delivery tube 718 with a flattened distal portion 710 and an opening 730 in the flattened distal portion for delivery of the magnetic bridle line 728. Further, the bridle device 700 comprises a spatula shaped retrieval member 720 with a flattened distal portion 716 and a retrieval magnet 708 disposed on the flattened distal portion. The flat, spatula shaped ends 710, 716 of the delivery tube 718 and the retrieval member 720 facilitate insertion through the nasal turbinates. Further, the flattened end 716 of the retrieval member 720 permits use of a retrieval magnet 708 having a larger surface area than other magnet shapes to facilitate connection to the magnetic bridle line 728.

The bridle device of the present application may be installed in a nasal tube prior to insertion of the nasal tube in the nose a person. For example, FIGS. 8A-8D illustrate the bridle device 400 installed in a delivery lumen of a nasal tube 800 according to an embodiment of the present application. However, any of the bridle devices of the present application may be installed or preloaded in a nasal tube. Further, the nasal tubes disclosed in U.S. patent application Ser. No. 13/839,012 may be used with the bridle device embodiments of the present application.

As illustrated in FIGS. 8A-8D, the nasal tube 800 has a proximal end 802 and a distal end 804, a retention flange 808, and a securing device 810. The nasal tube 800 comprises a main lumen extending from the proximal end 802 to the distal end 804 of the nasal tube. The nasal tube 800 also comprises at least one delivery lumen extending from the proximal end 802 and terminating at a delivery window or opening 806 in the outer wall of the nasal tube. As shown, the nasal tube 800 comprises a delivery window 806 on both sides of the nasal tube for insertion of the nasal tube and placement of the bridle using either nostril of the person.

Figure 8A:
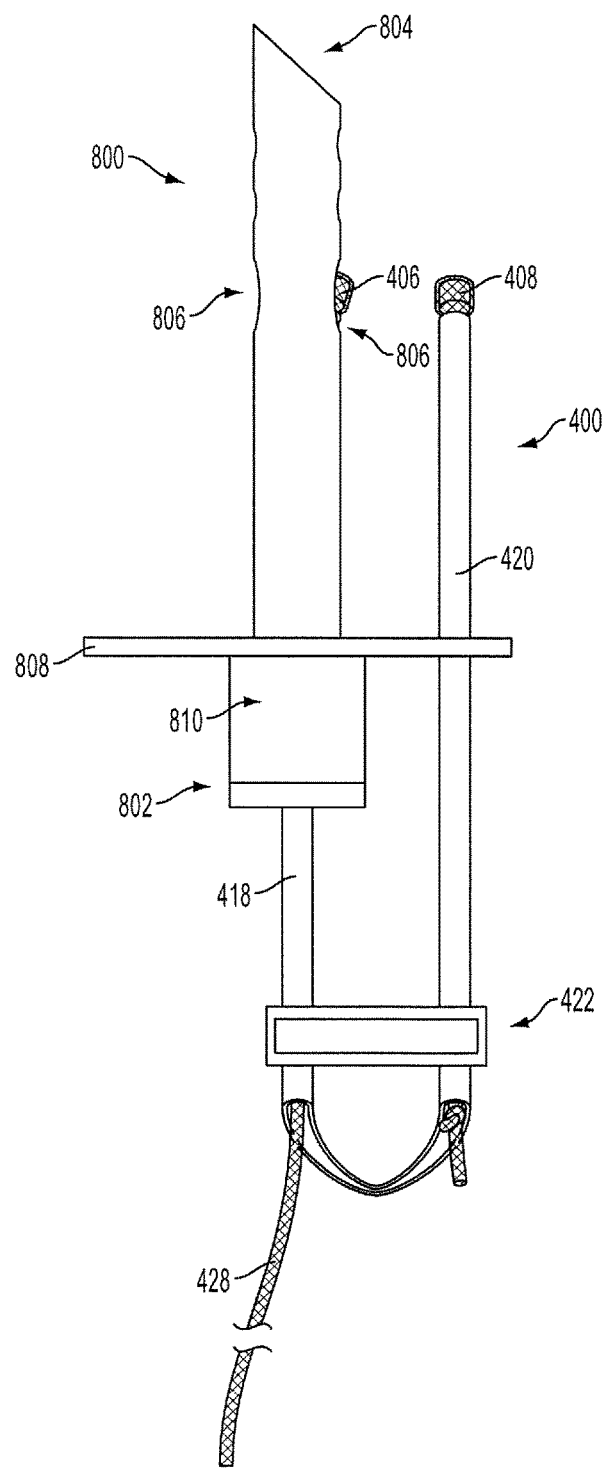
FIGS. 8A-8C are top views illustrating the placement of a bridle line using the bridle device of FIG. 4A installed in a nasal tube.
Figure 8B:
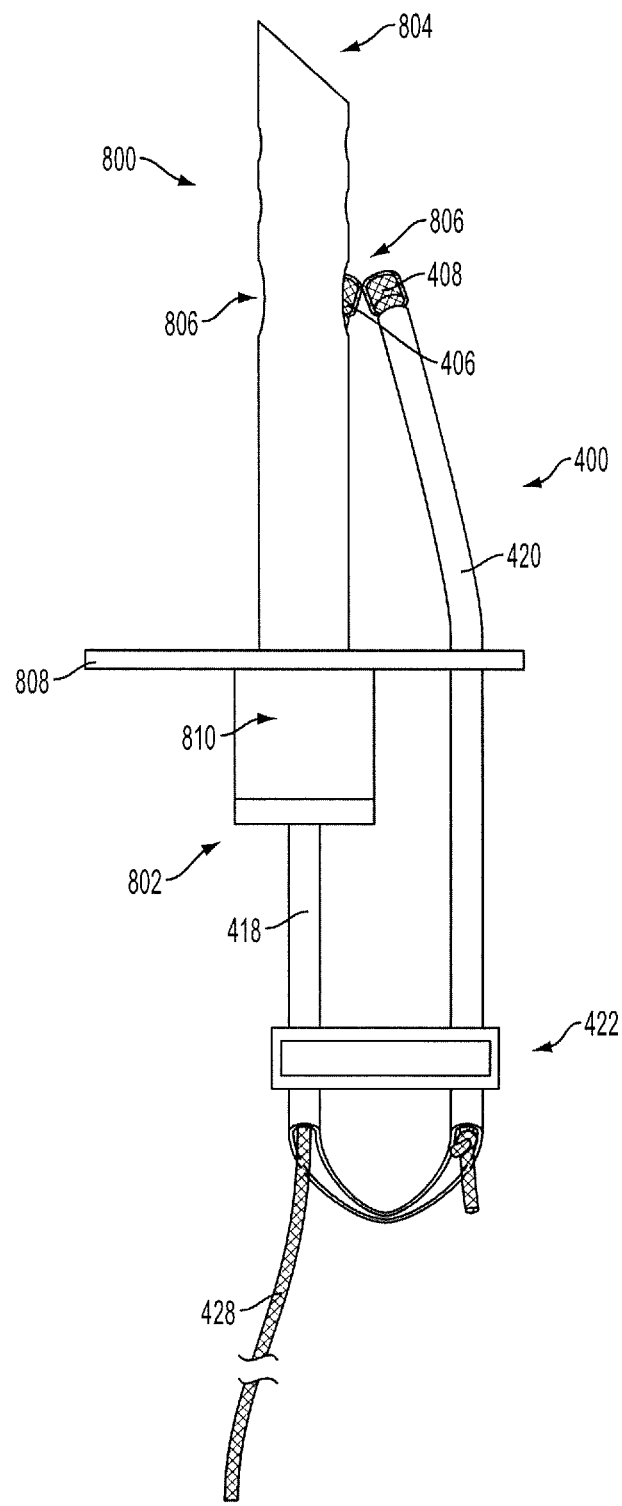
Figure 8C:
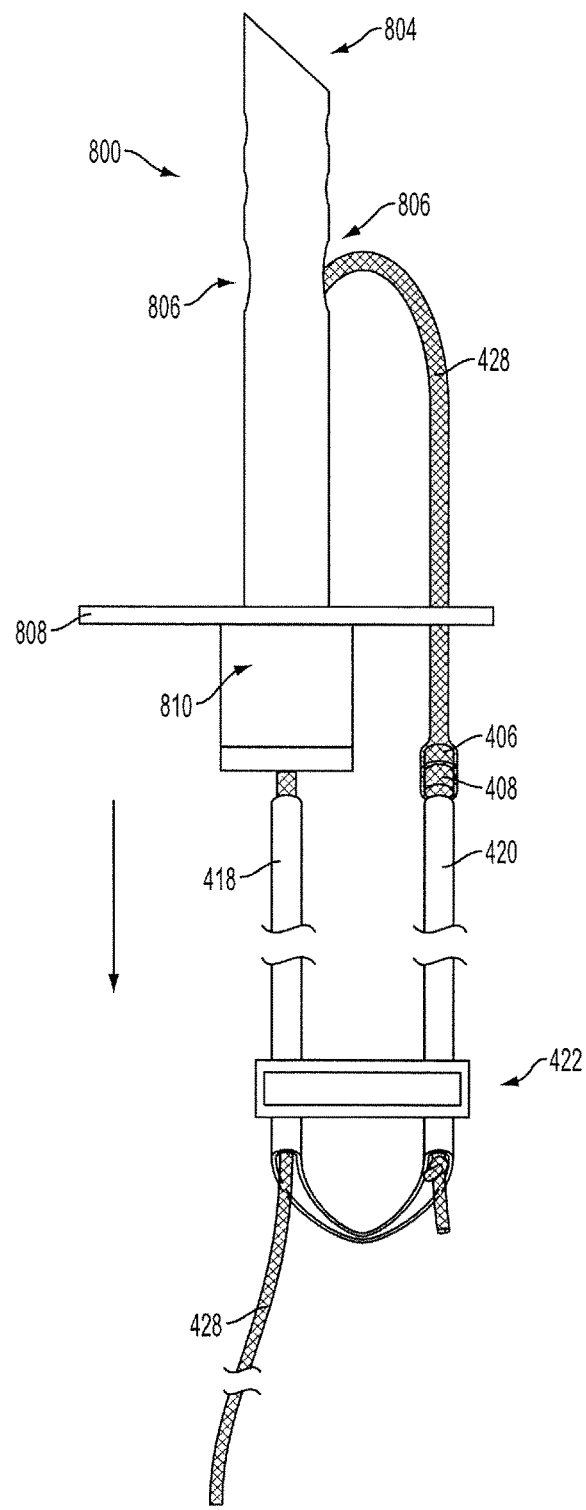
Figure 8D:
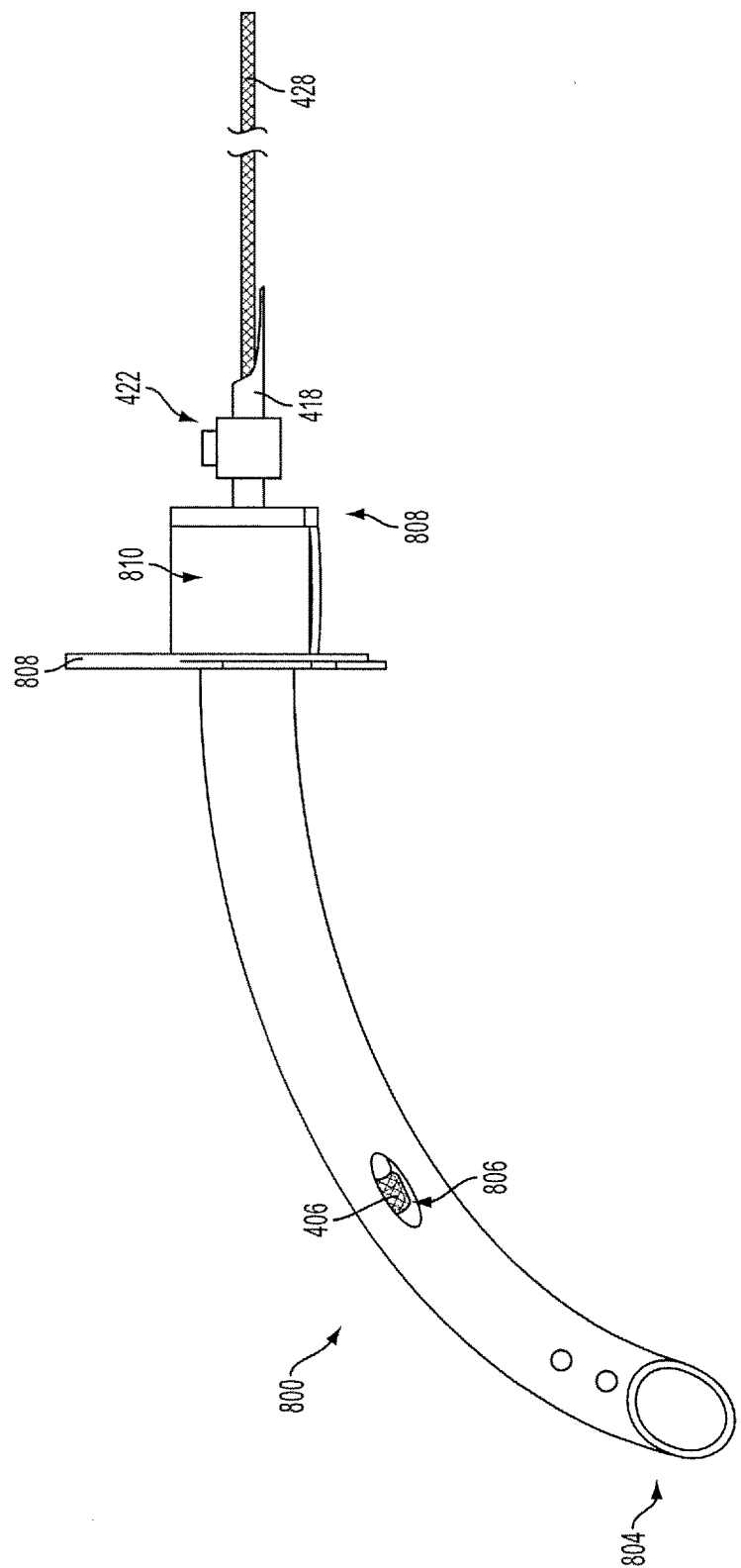
FIG. 8D is a side view of the bridle device of FIG. 4A installed in the nasal tube of FIGS. 8A-8C.

As illustrated in FIGS. 8A and 8D, the delivery tube 418 of the bridle device 400 is inserted in the delivery lumen such that the delivery magnet 406 is positioned in the delivery window 806. The nasal tube 800 is then advanced into a first nostril of the person and the retrieval tube 420 is advanced into a second nostril of the person. The nasal tube 800 is positioned such that the distal end 804 of the nasal tube terminates in a pharyngeal space of the person, such as for example, the oropharyngeal or largyngopharyngeal space of the person. Further, the delivery window 806 of the nasal tube 800 and the retrieval magnet 408 are positioned within the nasopharynx of the person.

As illustrated in FIGS. 8B and 8C, the delivery and retrieval magnets 406, 408 form a connection in the nasopharynx. The delivery tube 418 and the retrieval tube 420 are then retracted out of the nasopharynx, pulling the bridle line 428 out the delivery window 806 and around the vomer bone of the person. The bridle line 428 is also pulled out the second nostril of the person by removing the retrieval tube 420 from the second nostril. The delivery tube 418 is removed from the delivery lumen of the nasal tube 800. The delivery tube 418 slides over the bridle line 428 as the delivery tube is removed from the nasal tube 800.

The bridle line of the bridle device may be attached to the nasal tube in a variety of ways to secure the nasal tube to a person. For example, as illustrated in FIGS. 8A-8D, the nasal tube 800 comprises a securing device 810 for attaching the bridle line 428 to the nasal tube. As shown, the securing device 810 is a clip that surrounds the lumen of the nasal tube 800. The bridle line 428 may be placed between the clip and the lumen to attach the bridle line to the nasal tube 800. Further, the retention flange 808 of the nasal tube 800 may comprise an opening or other feature for attaching the bridle line 428 to the nasal tube. Further, any feature or combination of features of the nasal tubes and/or retention features disclosed in U.S. patent application Ser. No. 13/839,012 may be used with features or combinations of features of the bridle device embodiments of the present application. As such, bridle devices in accordance with the present invention may include any combination or subcombination of the features of the nasal tubes and/or retention features disclosed in U.S. patent application Ser. No. 13/839,012.

The present application also discloses a nasal tube capable of receiving a bridle line without the need for a traditional bridle clip. A clipless bridle system has many advantages. For example, the clipless bridle system does not include separate components that may accidently removed during a procedure. Also, a clipless bridle system makes adjustment and/or removal of the bridle line quick and easy for the caregiver.

The clipless nasal tube may be a variety of nasal tube types for nearly any medical purpose. For example, the nasal tube may be designed to terminate in the pharyngeal spaces of the person, such as the oropharyngeal or largyngopharyngeal space of the person. As another example, the nasal tube may be designed to extend into the esophagus of the person and terminate in the alimentary tract to aid in nutrient delivery, drug delivery, endoscopy, decompression, etc. The nasal tube may also be designed to terminate in the bronchi or the lungs. Further, the nasal tube may be a variety of sizes for various applications, such as biopsy in both adult and pediatric populations.

The clipless nasal tube of the present application may comprise one or more grooves for receiving a bridle line. The grooves may be parallel, angled, or perpendicular to one another to allow for wrapping the bridle line repeatedly over itself within the groove depending upon the required amount of friction. The grooves may be located within the body of the tube wall or within a flange of the tube.

Figure 9A:
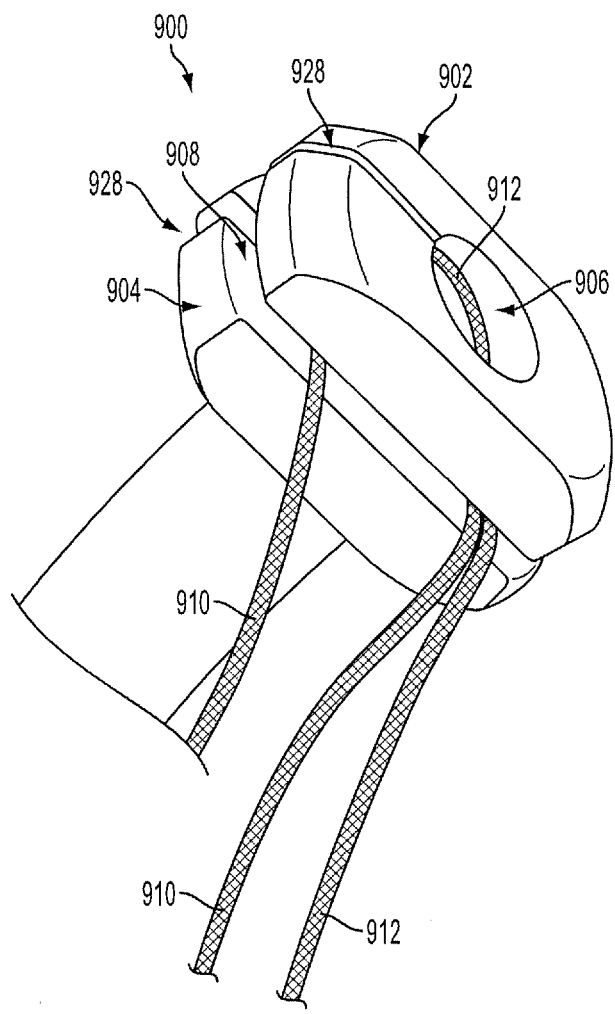
FIG. 9A is a perspective view of a nasal tube according to an embodiment of the present application.
Figure 9B:
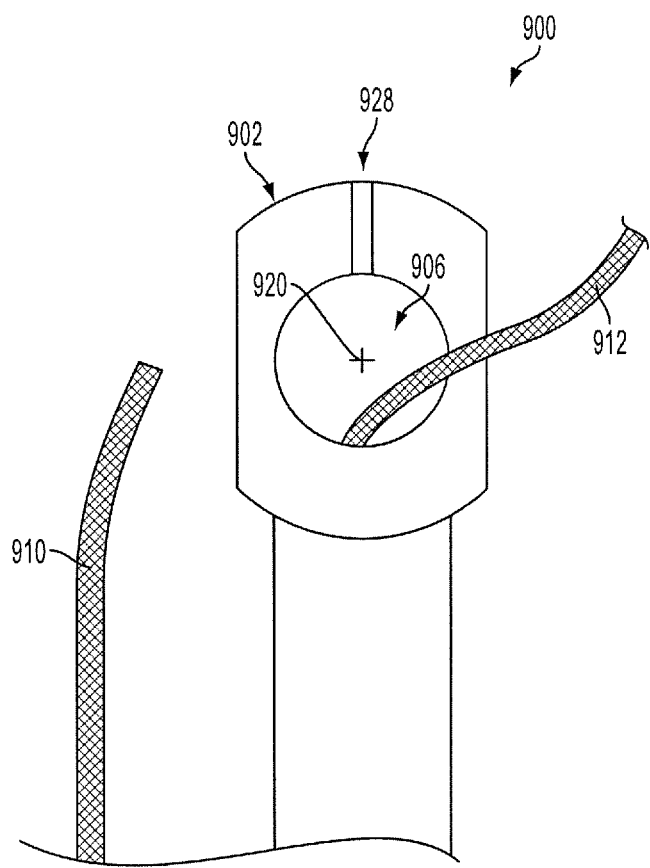
FIGS. 9B and 9C are front views of the nasal tube of FIG. 9A illustrating the attachment of bridle lines to the nasal tube.
Figure 9C:
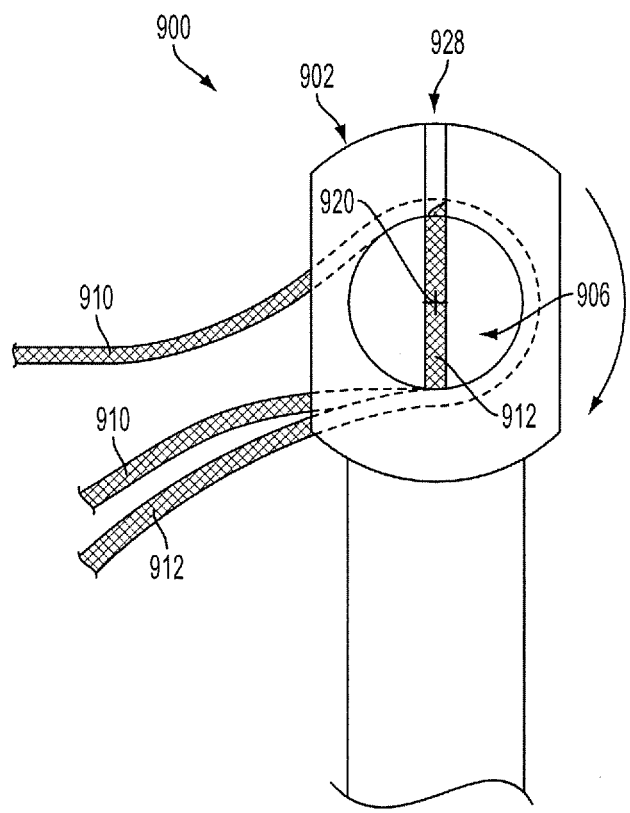

FIGS. 9A-9C illustrate a nasal tube 900 according to an embodiment of the present application. As shown, the nasal tube 900 comprises first and second flange portions 902, 904 positioned at or near the proximal end of the nasal tube and about the main lumen 906 of the nasal tube. The flange portions 902, 904 form a channel 908 that circumferentially surrounds the main lumen 906 about a longitudinal axis 920 of the main lumen. The first and second flange portions 902, 904 each comprise a slot, slit, channel, or opening 928 that extends radially from the main lumen 906 to the outer edge of each flange portion. As shown, the slots 928 of the first and second flange portions 902, 904 are substantially vertical and substantially aligned. However, in other embodiments, one or both of the flange portions 902, 904 may or may not comprise a slot 928 and the slots may or may not be substantially vertical or aligned. Further, the flange portions 902, 904 may or may not be adjustable over the tube's length. The nasal tube 900 may also have some reinforcement around the main lumen 906 in the bottom of the channel such that a secure constricting knot or wrap of a bridle line may be used without risk of collapsing the lumen.

As illustrated in FIGS. 9A-9C, a first bridle line 910 may be attached to the nasal tube 900 by wrapping the bridle line around the main lumen 906 between the first and second flange portions 902, 904 and in the channel 908. Further, the slots 928 may be used provide access to the channel 908 for bridle lines extending from the main lumen 906, proximal and distal ends of the nasal tube 900. For example, as shown, a second bridle line 912 extending from the main lumen 906 of the nasal tube 900 may be attached to the nasal tube by placing the bridle line through the slot 928 in the first flange portion 902 and then wrapping the bridle line around the main lumen between the first and second flange portions 902, 904 and in the channel 908. However, the first and second flange portions 902, 904 may be used to attach a bridle line to the nasal tube 900 in a variety of different ways.

Figure 10A:
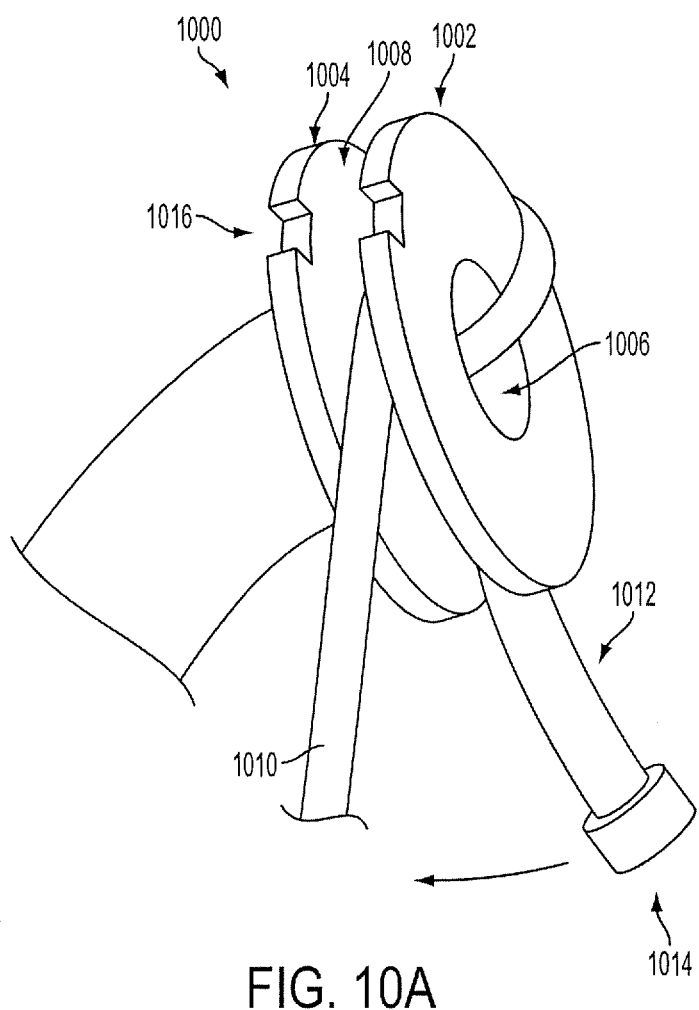
FIGS. 10A and 10B are perspective views of a nasal tube according to an embodiment of the present application illustrating the attachment of a bridle line to the nasal tube.
Figure 10B:
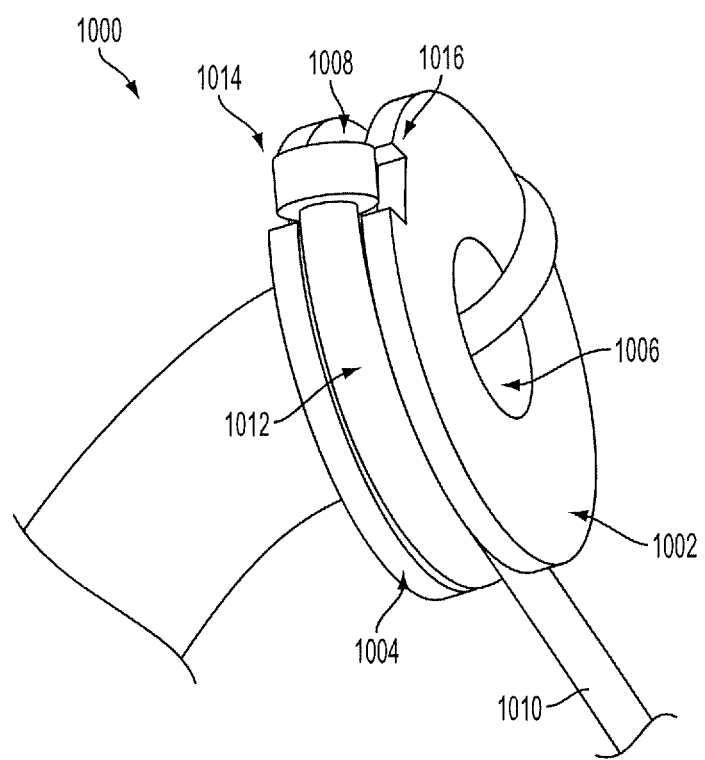

FIGS. 10A and 10B illustrate a nasal tube 1000 according to an embodiment of the present application. As shown, the nasal tube 1000 comprises first and second flange portions 1002, 1004 positioned at or near the proximal end of the nasal tube and about the main lumen 1006 of the nasal tube. The flange portions 1002, 1004 form a channel 1008 that circumferentially surrounds the main lumen 1006. As shown, a bridle line 1010 is wrapped around the main lumen 1006 between the first and second flange portions 1002, 1004 and in the channel 1008. A friction member may be received in the channel 1008 to secure the bridle line 1010 in the channel. As shown, the friction member is an arm 1012 which extends out from the body of the tube 1000, is pliable and elastic, and wraps over the top of the bridle line 1010 as it lays in the channel 1008.

As illustrated in FIGS. 10A and 10B, the arm 1012 has a distal end or head 1014 with a larger diameter than the remainder of the arm. The enlarged end 1014 fits into notches 1016 in the first and second flange portions 1002, 1004 to hold the arm firmly in place over top of the bridle line 1010. When the friction member is tensioned and positioned over top of the bridle line 1010, it increases the total friction of the bridle line on the tube 1000 and secures the bridle line to the tube.

Another embodiment of a clipless nasal tube which can be used in conjunction with a bridle system includes a hole or void (e.g., a notch, slit, slot, channel, opening, or the like) in the body or a flange of a nasal tube. The bridle line is threaded through the void and therefore, the bridle may be completely unwedded from the tube, yet later wedded to the tube via the void. Beads or knots may be added to the bridle line above and below the void. Further, a frictional member, such as a plug, screw or cap which is attached and a part of the tube (like the frictional member described above) may be inserted into the void with the passing bridle line so that that when in place, the bridle line will be fixed and retained to the tube. The friction member in this case will function by mechanical interference and/or friction with the edges of the void, thereby creating intense friction with the bridle line which is positioned between the fiction member and the edges of the void. Further, the bridle line need not be threaded through the void entirely, but a "bite" of bridle line may be threaded through the void which would subsequently communicate with the tube and friction member in two places. The friction member may also have an anchor on its superior surface to wrap or otherwise secure the bridle line for increased security, access and organization.

The clipless nasal tube design of the present application may be used with any nasal tube that requires a secure retention, such as, for example, nasogastric tubes, endotracheal tubes, nasal tubes configured to conduct oxygen and/or remove carbon dioxide, and nasal tubes configured as an anesthesiology monitoring or oxygen delivery device.

As described herein, when one or more components are described as being connected, joined, affixed, coupled, attached, or otherwise interconnected, such interconnection may be direct as between the components or may be in direct such as through the use of one or more intermediary components. Also as described herein, reference to a "member," "component," or "portion" shall not be limited to a single structural member, component, or element but can include an assembly of components, members or elements.

While the present invention has been illustrated by the description of embodiments thereof, and while the embodiments have been described in considerable detail, it is not the intention of the applicants to restrict or in any way limit the scope of the invention to such details. Additional advantages and modifications will readily appear to those skilled in the art. For example, where components are releasably or removably connected or attached together, any type of releasable connection may be suitable including for example, locking connections, fastened connections, tongue and groove connections, etc. Still further, component geometries, shapes, and dimensions can be modified without changing the overall role or function of the components. Therefore, the inventive concept, in its broader aspects, is not limited to the specific details, the representative apparatus, and illustrative examples shown and described. Accordingly, departures may be made from such details without departing from the spirit or scope of the applicant's general inventive concept.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

We claim:

1. A bridle device, comprising:
a retrieval portion having a retrieval member and a retrieval magnet attached to the retrieval member; and
a delivery portion having a delivery member and a delivery magnet that is movable relative to a distal portion of the delivery member;
wherein the delivery member is a delivery tube and the delivery magnet is attached to a flexible elongated member received in the delivery tube, and wherein a wall of the delivery tube is separated or configured to be separated along a length of the delivery tube such that the separated delivery tube wall creates an opening that permits the elongated member to be removed from within the delivery tube.

2. The bridle device of claim 1, wherein the delivery magnet is positioned outside the delivery tube and is movable relative to a distal end of the delivery tube.

3. The bridle device of claim 2, wherein the delivery magnet is rotatable relative to a distal end of the delivery tube and about a longitudinal axis of the delivery tube.

4. The bridle device of claim 2, wherein both poles of the delivery magnet are exposed outside of the delivery tube.

5. The bridle device of claim 2 further comprising a delivery stop that is configured to maintain tension on the elongated member received in the delivery tube as the delivery tube is inserted into the nose of the person.

6. The bridle device of claim 1, wherein the retrieval magnet is fixed at a distal end of the retrieval member.

7. The bridle device of claim 6, wherein one pole of the retrieval magnet is exposed outside the retrieval member and one pole of the retrieval magnet is received in the retrieval member.

8. The bridle device of claim 1, wherein the retrieval member is a retrieval tube and the retrieval magnet is attached to a flexible elongated member received in the retrieval tube, and wherein the retrieval magnet is positioned outside the retrieval tube and is movable relative to a distal portion of the retrieval tube.

9. The bridle device of claim 8, wherein the retrieval magnet is rotatable relative to a distal end of the retrieval tube and about a longitudinal axis of the retrieval tube.

10. The bridle device of claim 8, wherein both poles of the retrieval magnet are exposed outside of the retrieval tube.

11. The bridle device of claim 1, wherein at least a portion of the delivery portion is connected to at least a portion of the retrieval portion.

12. The bridle device of claim 11, wherein the bridle device is U-shaped with the retrieval portion forming a first side of the U and the delivery portion forming a second side of the U.

13. The bridle device of claim 12, wherein the delivery magnet is positioned outside the delivery tube and is movable relative to the distal portion of the delivery tube, and wherein the retrieval member is a retrieval tube and the retrieval magnet is attached to a second flexible elongated member received in the retrieval tube, and wherein the retrieval magnet is positioned outside the retrieval tube and is movable relative to a distal portion of the retrieval tube.

14. The bridle device of claim 12, wherein the retrieval portion and the delivery portion are removably connected together by a handle, and wherein the handle comprises channels configured to receive the retrieval portion and the delivery portion.

15. A bridle device, comprising:
a retrieval portion having a retrieval member and a retrieval magnet attached to the retrieval member; and
a delivery portion having a delivery tube and a delivery magnet attached to a flexible elongated member received in the delivery tube, wherein the delivery magnet is movable relative to a distal portion of the delivery tube;
wherein the retrieval member and the delivery tube form a U-shape, wherein the retrieval member forms a first side of the U and the delivery tube forms a second side of the U, wherein the U-shape permits simultaneous insertion of the retrieval member and the delivery tube into nostrils of a patient.

16. The bridle device of claim 15, wherein both poles of the delivery magnet are exposed outside of the delivery tube.

17. The bridle device of claim 15, wherein the retrieval portion and the delivery portion are removably connected together by a handle.

18. The bridle device of claim 15, wherein a wall of the delivery tube is separated or configured to be separated along a length of the delivery tube such that the separated delivery tube wall creates an opening that permits the elongated member to be removed from within the delivery tube.

19. The bridle device of claim 15, wherein the delivery member is a delivery tube and the delivery magnet is attached to a flexible elongated member received in the delivery tube, and wherein a wall of the delivery tube is separated or configured to be separated along a length of the delivery tube such that the separated delivery tube wall creates an opening that permits the elongated member to be removed from within the delivery tube.

20. A bridle device, comprising:
a retrieval portion having a retrieval member and a retrieval magnet attached to the retrieval member; and
a delivery portion having a delivery member and a delivery magnet attached to a distal portion of the delivery member, wherein the retrieval portion and the delivery portion are connected together by a handle, and wherein the handle is configured such that the delivery magnet and the retrieval magnet are capable of being simultaneously inserted into nostrils of a patient.

21. The bridle device of claim 20, wherein the delivery magnet is shaped as a polyhedron.

22. The bridle device of claim 20, wherein the retrieval member and the delivery member form a U-shape, wherein the retrieval member forms a first side of the U and the delivery member forms a second side of the U.

23. A bridle device, comprising:
a retrieval portion having a retrieval member and a retrieval magnet attached to the retrieval member;
a delivery portion having a delivery member and a delivery magnet that is movable relative to a distal portion of the delivery member;
wherein at least a portion of the delivery portion is connected to at least a portion of the retrieval portion;
wherein the bridle device is U-shaped with the retrieval portion forming a first side of the U and the delivery portion forming a second side of the U; and
wherein the retrieval portion and the delivery portion are removably connected together by a handle, and wherein the handle comprises channels configured to receive the retrieval portion and the delivery portion.

24. A bridle device, comprising:
a retrieval portion having a retrieval member and a retrieval magnet attached to the retrieval member; and
a delivery portion having a delivery member and a delivery magnet that is movable relative to a distal portion of the delivery member, wherein a proximal portion of the delivery member is connected to a proximal portion of the retrieval member, wherein the connection between the proximal portion of the delivery member and the proximal portion of the retrieval member permits simultaneous insertion of the delivery portion and the retrieval portion into nostrils of a patient.

25. The bridle device of claim 24, wherein the delivery portion and the retrieval portion are connected together by a handle.

26. The bridle device of claim 24, wherein the retrieval member and the delivery member are formed from a single U-shaped piece, wherein the retrieval member forms a first side of the U and the delivery member forms a second side of the U.

27. The bridle device of claim 24, wherein the delivery member is a delivery tube and the delivery magnet is attached to a flexible elongated member received in the delivery tube.

28. The bridle device of claim 27, wherein a wall of the delivery tube is separated or configured to be separated along a length of the delivery tube such that the separated delivery tube wall permits the elongated member to be removed from within the delivery tube.

29. The bridle device of claim 27, wherein the delivery magnet is movable relative to the distal portion of the delivery tube and both poles of the delivery magnet are exposed outside of the delivery tube.

30. The bridle device of claim 27, wherein the delivery magnet is rotatable relative to a distal portion of the delivery tube and about a longitudinal axis of the delivery tube.

31. The bridle device of claim 27 further comprising a delivery stop that is configured to maintain tension on the elongated member received in the delivery tube as the delivery tube is inserted into a nostril of the patient.

* * * * *